United States Patent
LaVoie et al.

(10) Patent No.: US 9,822,108 B2
(45) Date of Patent: Nov. 21, 2017

(54) ANTIMICROBIAL AGENTS

(71) Applicant: RUTGERS, THE STATE UNIVERSITY OF NEW JERSEY, New Brunswick, NJ (US)

(72) Inventors: Edmond J. LaVoie, New Brunswick, NJ (US); Ajit Parhi, New Brunswick, NJ (US); Daniel S. Pilch, New Brunswick, NJ (US); Malvika Kaul, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/371,950

(22) PCT Filed: Jan. 11, 2013

(86) PCT No.: PCT/US2013/021295
§ 371 (c)(1),
(2) Date: Jul. 11, 2014

(87) PCT Pub. No.: WO2013/106756
PCT Pub. Date: Jul. 18, 2013

(65) Prior Publication Data
US 2014/0350024 A1    Nov. 27, 2014

Related U.S. Application Data

(60) Provisional application No. 61/586,583, filed on Jan. 13, 2012.

(51) Int. Cl.
| | |
|---|---|
| *A61K 31/495* | (2006.01) |
| *C07D 471/04* | (2006.01) |
| *A61K 31/4375* | (2006.01) |
| *A61K 31/498* | (2006.01) |
| *C07D 237/30* | (2006.01) |
| *C07D 239/74* | (2006.01) |
| *C07D 241/42* | (2006.01) |
| *C07D 241/44* | (2006.01) |

(52) U.S. Cl.
CPC ........ *C07D 471/04* (2013.01); *A61K 31/4375* (2013.01); *A61K 31/498* (2013.01); *C07D 237/30* (2013.01); *C07D 239/74* (2013.01); *C07D 241/42* (2013.01); *C07D 241/44* (2013.01)

(58) Field of Classification Search
CPC ................................................. A61K 31/498
USPC ........................................................ 514/249
See application file for complete search history.

(56) References Cited

U.S. PATENT DOCUMENTS

| | | | |
|---|---|---|---|
| 2,748,118 A * | 5/1956 | Druey et al. | ......... C07D 241/42 544/353 |
| 4,309,539 A | 1/1982 | Boller et al. | |
| 4,782,058 A | 11/1988 | Griffith | |
| 4,826,990 A | 5/1989 | Musser et al. | |
| 5,077,142 A | 12/1991 | Sakon et al. | |
| 5,177,067 A | 1/1993 | Guerry et al. | |
| 5,177,075 A | 1/1993 | Suto et al. | |
| 8,088,791 B2 | 1/2012 | Brown et al. | |
| 8,415,383 B2 | 4/2013 | Haydon et al. | |
| 8,492,414 B2 | 7/2013 | Haydon et al. | |
| 8,865,736 B2 | 10/2014 | Brown et al. | |
| 8,933,096 B2 | 1/2015 | LaVoie et al. | |
| 2002/0035090 A1 | 3/2002 | Zeldis et al. | |
| 2002/0040147 A1 | 4/2002 | Hammond et al. | |
| 2002/0055516 A1 | 5/2002 | Miyazaki et al. | |
| 2002/0077333 A1 | 6/2002 | Dey et al. | |
| 2003/0181519 A1 | 9/2003 | Mewshaw et al. | |
| 2005/0043300 A1 | 2/2005 | Middleton et al. | |
| 2006/0183943 A1 | 8/2006 | Hu | |
| 2008/0027028 A1 | 1/2008 | Chichak | |
| 2008/0300239 A1 | 12/2008 | Adams et al. | |
| 2009/0076074 A1 | 3/2009 | Jung et al. | |

(Continued)

FOREIGN PATENT DOCUMENTS

| | | |
|---|---|---|
| DE | 4327748 A1 | 2/1995 |
| EP | 0719764 A1 | 7/1996 |

(Continued)

OTHER PUBLICATIONS

Metzner et al. "Antimicrobial Activity of selected quinoxalines," Pharmazie, 1981, vol. 36, No. 5, pp. 368-370.*
Metzner et al. "Antimicrobial Activity of selected quinoxalines," Pharmazie, 1981, vol. 36, No. 5, pp. 368-370 (with English Translation.*
Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", *Bull. Chem. Soc. Japan*, 57 (8), 2188-2192 (1984).
Augstein et al., "Synthesis of 11-Hydroxy-2,3,9,10-tetramethoxy-5,6,13,13a-tetrahydro-8H-dibenzo[a,g]quinolizine. A Contribution to the Structure of Stepharotine", *Stepharotine*, vol. 34, No. 5, 1349-1352 (1969).
Bayer et al., "Pyridyl-substituierte Tetralonderivate: Eine neue Klasse nichtsteroidaler Aromatase-Inhibitoren", *Arch. Pharm.* 324, 815-820 (1991). [English Abstract].

(Continued)

*Primary Examiner* — Shengjun Wang
(74) *Attorney, Agent, or Firm* — Viksnins Harris Padys Malen LLP

(57) ABSTRACT

The invention provides methods of treating a bacterial infection in a mammal comprising administering to the mammal a substituted bicyclic heteroaromatic ring compound of formula I: wherein two of $X_1$ to $X_8$ are N and the remaining of $X_1$ to $X_8$ are CH; or a pharmaceutically acceptable salt thereof, as well as novel compounds of formula I and salts thereof and pharmaceutical compositions comprising a compound of formula I or a pharmaceutically acceptable salt thereof.

(I)

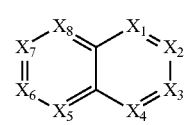

12 Claims, No Drawings

(56) References Cited

U.S. PATENT DOCUMENTS

| | | | |
|---|---|---|---|
| 2009/0312319 | A1 | 12/2009 | Ren et al. |
| 2010/0120810 | A1 | 5/2010 | Leblond et al. |
| 2012/0022061 | A1 | 1/2012 | LaVoie |
| 2013/0109713 | A1 | 5/2013 | LaVoie et al. |
| 2013/0116278 | A1 | 5/2013 | LaVoie |
| 2014/0135332 | A1 | 5/2014 | Haydon et al. |
| 2015/0011559 | A1 | 1/2015 | LaVoie et al. |
| 2015/0031694 | A1 | 1/2015 | LaVoie et al. |
| 2015/0133465 | A1 | 5/2015 | LaVoie et al. |

FOREIGN PATENT DOCUMENTS

| | | |
|---|---|---|
| EP | 1078920 A1 | 2/2001 |
| EP | 1724262 A1 | 11/2006 |
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 2004/000814 A1 | 12/2003 |
| WO | WO 2004/005472 A2 | 1/2004 |
| WO | WO 2004/018414 A2 | 3/2004 |
| WO | WO 2004/041210 A2 | 5/2004 |
| WO | WO 2004/073709 A1 | 9/2004 |
| WO | WO 2004/087145 A2 | 10/2004 |
| WO | WO 2005/075428 A1 | 8/2005 |
| WO | WO 2005/097100 A2 | 10/2005 |
| WO | WO 2006/067048 A1 | 6/2006 |
| WO | WO 2006/105289 A1 | 10/2006 |
| WO | WO 2007/107758 A1 | 9/2007 |
| WO | WO 2007/148093 A1 | 12/2007 |
| WO | WO 2008/016596 A2 | 2/2008 |
| WO | WO 2009/037485 A1 | 3/2009 |
| WO | WO 2009/040507 A1 | 4/2009 |
| WO | WO 2009/074810 A1 | 6/2009 |
| WO | WO 2009/074812 A1 | 6/2009 |
| WO | WO 2010/127307 A1 | 11/2010 |
| WO | WO 2011/112435 A1 | 9/2011 |
| WO | WO 2011/156626 A1 | 12/2011 |
| WO | WO 2012/142671 A1 | 10/2012 |

OTHER PUBLICATIONS

Bedi et al., "Synthesis and biological activity of novel antibacterial quinazolines", *Bioorganic & Medicinal Chemistry Letters* 14, 5211-5213 (2004).
Beilstein, Database Beilstein Institute for Organic Chemistry, XP002591901, Database Accession No. 3834367 (BRN) abstract (1918).
Beilstein, Database Beilstein Institute for Organic Chemistry, XP002591900, Database Accession No. 3837583(BNR) abstract (1930).
Beuria, T.K. et al., "Sanguinarine Blocks Cytokinesis in Bacteria by Inhibiting FtsZ Assembly and Bundling", Biochemistry, 44, 16584-16593 (2005).
Bild et al., "Discovery of Inhibitors of MCF-7 Tumor Cell Adhesion to Endothelial Cells and Investigation on their Mode of Action", *Arch. Pharm. Med. Chem.*, 337, 687-694 (2004).
Chen et al., "Synthesis and Antibacterial Evaluation of Certain Quinolone Derivatives", *J. Med. Chem.*, 44, 2374-2377 (2001).
Cole et al., "Potential Tumor-Selective Nitroimidazolylmethyluracil Prodrug Derivatives: Inhibitors of the Angiogenic Enzyme Thymidine Phosphorylase", J. Med. Chem., 46, 207-209 (2003).
Database Registry [Online], Chemical Abstracts Service, XP002570845, Database accession No. 1043562-34-0/RN, abstract (2008).
Denes et al., "The chemistry of sanguinarine", XP002570844, Chemical Abstracts Service, Database accession No. 1960:91836, abstract, *Magyar Kemiai Folyoirat*, 64, 125-130 (1958).
Dyke et al., "The Chemistry of Cryptopine—I The Epicryptopines", *Tetrahedr0n*, vol. 24, No. 3, 1455-1465 (1968).
Dyke et al., "The Chemistry of Cryptopine—II Pseudocryptopine Chloride", *Tetrahedron*, vol. 25, 5375-5381 (1969).

Dykhuizen, "Santa Rosalia revisited: Why are there so many species of bacteria?", *Antonie van Leeuwenhock*, 73, 25-33 (1998).
Foroumadi et al., "Synthesis and in vitro antibacterial evaluation of N-[5-(5-nitro-2-thienyl)-1,3,4-thiadiazole-2-yl] piperazinyl quinolones", *European Journal of Medicinal Chemistry*, 38, 851-854 (2003).
Gopinath et al., "Dehydrogenation cyclization of 2-aryl-1-tetralone oxime acetates", XP002570843, Chemical Abstracts Service, Database accession No. 1960:23123, abstract, *Current Science*, 28, 241-242 (1959).
Huecas et al., "Protein Structure and Folding: The Interactions of Cell Division Protein FtsZ with Guanine Nucleotides", *J. Biol. Chem.*,282, 37515-37528 (2007).
Huttunen et al., "Prodrugs—An Efficient Way to Breach Delivery and Targeting Barriers", *Current Topics in Medicinal Chemistry* 11, 2265-2287 (2011).
Ishii et al., "Studies on the Chemical Constituents of Rutaceous Plants. LV.1 The Development of a Versatile Mehtod for the Synthesis of Antitumor-Active Benzo[c]phenanthridine Alkaloids. (5).1 A New Method for Quaternization of the Benzo[c]phenanthridine Nucleus", *Chem. Pharm. Bull.*, 32(a), 2984-2994 (1984).
Ito et al., "A medium-term rat liver bioassay for rapid in vivo detection of carcinogenic potential of chemicals", *Cancer Sci*, vol. 94 (1), 3-8 (2003).
Jackson et al., "Non-Steroidal Aromatase Inhibitors Based on a Biphenyl Scaffold: Synthesis, in vitro SAR, and Molecular Moedelling", *Chem Med Chem* 3, 603-618.
Jaiswal et al., "Totarol inhibits bacterial cytokinesis by perturbing the assembly dynamics of FtsZ", *Biochemistry*, vol. 46(14), 4211-4220 (2007).
Kaul et al., "A Bactericidal Guanidinomethyl Biaryl That Alters the Dynamics of Bacterial FtsZ Polymerization", *Journal of Medicinal Chemistry*, 55, 10160-10176.
Leroux et al., "N-(4-Biphenylmethyl)imidazoles as Potential Therapeutics for the Treatment of Prostate Cancer: Metabolic Robustness Due to Fluorine Substitution?", *Helvetica Chimica Acta*, vol. 86, 2671-2686 (2003).
Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", *J. Med. Chem.* 33, 24-245 (1990).
Nicolson et al., "Potentiation of methicillin activity against methicillin-resistant *Staphylococcus aureus* by diterpenes", *FEMS Microbiology Letters* 179, 233-239.
Okudaira et al., "A Study of the Intestinal Absorption of an Ester-Type Prodrug, ME3229, in Rats: Active Efflux Transport as a Cause of Poor Bioavailability of the Active Drug", *Journal of Pharmacology and Experimental Therapeutics*, vol. 294 (2), 580-587 (2000).
Patent Cooperation Treaty, International Searching Authority, Search Report and Written Opinion for PCT/US2013/021295, 14 pages, dated Jul. 19, 2013.
Roesch et al., "Synthesis of isoquinolines and pyridines by the palladium-catalyzed iminoannulation of internal alkynes", *J. Org. Chem.* 66, 8042-8051 (2001).
Sanders et al., "Selective Cytotoxicity of Topoisomerase-Directed Protoberberines against Glioblastoma Cells", *Biochemical Pharmacology*, vol. 56, 1157-1166 (1998).
Schonenberger, "Synthesis and Pharmacological Test of N-(3'-Methoxy-benzamidomethyl)-D-norephedrine and Analogous Compounds", *Arch. Pharm* 309, 289-301 (1976). [English Abstract].
Sethi, "Enzyme Inhibition VIII: Mode of Inhibition of Reverse Transcriptase Activity by Analogues, Isomers, and Related Alkaloids of Coralyne", *Journal of Pharmaceutical Sciences*, vol. 74 (1), 889-891 (1985).
Singh et al., "Structure—Activity Relationship Studies Leading to the Identification of (2E)-3-[I-[(2,4-Dichlorophenyl)methyl]-5-fluoro-3-methyl-1H-indol-7-yl]-N-[(4,5-dichloro-2-thienyl)sulfonyl]-2-propenamide (DG-041), a Potent and Selective Prostanoid EP3 Receptor Antagonist, as a Novel Antiplatelet gent that Does not Prolong Bleeding", *J. Med. Chem.* 53, 18-36 (2010).

(56) References Cited

OTHER PUBLICATIONS

Wachall et al., "Imidazole Substituted Biphenyls: A New Class of Highly Potent and in Vivo Active Inhibitors of P450 17 as Potential Therapeutics for Treatment of Prostate Cancer", *Bioorganic & Medicinal Chemistry* 7, 1913-1924 (1999).

Wigbers et al., "Synthesis, Structures, and Aggregation Properties of N-Acylamidines", *Eur. J. Org. Chem.*, 861-877 (2011).

Wu et al., "Regulatory perspectives of Type II prodrug development and time-dependent toxicity management: Nonclinical Pharm/Tox analysis and the role of comparative toxicology", *Toxicology* 236, 1-6 (2007).

Yaeko et al., "Studies on the constituents of Bocconia Cordata. IV. Transformation of sanguinarine into bocconine", XP002570841, Chemical Abstracts Service, Database accession No. 1992:129332, abstract, *Journal of Heterocyclic Chemistry*, 28(8), 1841-1843 (1991).

Yamaguchi et al., "Utilization of Protopine and Related Alkaloids. XIV. Oxidation of the Photo-adduct of 1-Oxoanhydromethylberberine with Nitrosobenzene, and Synthesis Ring C-Substituted Benzo [c]phenanthridines", *Chem. Pharm. Bull.*, 31(5), 1601-1611 (1983).

\* cited by examiner

ANTIMICROBIAL AGENTS

PRIORITY OF INVENTION

This application claims priority from U.S. Provisional Application No. 61/586,583 filed 13 Jan. 2012, which application is incorporated by reference.

BACKGROUND OF THE INVENTION

The emergence of Multidrug Resistant (MDR) bacterial pathogens (e.g. methicillin-resistant *Staphylococcus aureus* (MRSA), *Acinetobacter baumannii-calcoaceticus* complex (ABC), etc.) has increased concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need for additional antimicrobials. In this connection, there is a pressing need for new antibiotics that exhibit novel mechanisms of action or that are able to circumvent known resistance pathways.

Elements of the bacterial cell division machinery present targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

SUMMARY OF THE INVENTION

In one embodiment the invention provides compounds that display antimicrobial activity. Accordingly, the invention provides a method for treating a bacterial infection in a mammal comprising administering to the mammal an effective amount of a bicyclic heteroaromatic ring compound of formula I:

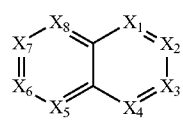

(I)

wherein:
two of $X_1$ to $X_8$ are N and the remaining of $X_1$ to $X_8$ are CH; and
the bicyclic heteroaryl ring is a) substituted on a first ring carbon with a group $R^1$ and substituted on a second ring carbon with a group $R^2$; or is b) substituted on a ring carbon with a group $R^1$ and substituted on a ring nitrogen with $R^3$ to form the corresponding ammonium salt that has a suitable counter ion $X^-$; or is c) substituted on a ring carbon with a group $R^4$;

$R^1$ is phenyl that is optionally substituted with one or more groups independently selected from halo, $(C_1-C_6)$ alkyl, $(C_3-C_6)$cycloalkyl, $(C_1-C_6)$alkoxycarbonyl, $-C(=O)NR^eR^f$, and phenyl that is optionally substituted with one or more halo, $(C_1-C_6)$alkyl, or $(C_3-C_6)$cycloalkyl;

$R^2$ is $-NR^cR^d$, $-N^+(R^a)_3Z^-$, $-C(=NR^a)-NR^cR^d$, $-NR^a-C(=NR^a)-NR^cR^d$, $-NR^a-C(=NR^a)-R^a$, $-NR^a-NR^a-C(=NR^a)-NR^cR^d$, $-C(H)=N-NR^a-C(=NR^a)-NR^cR^d$, $-C(=O)-NR^a-C(=NR^a)-NR^cR^d$, $-C(=O)-NR^a-C(=NR^a)-R^a$, or $R^b$; or $R^2$ is $(C_1-C_6)$alkyl that is substituted with $-NR^cR^d$, $-N^+(R^a)_3Z^-$, $-C(=NR^a)-NR^cR^d$, $-NR^aC(=NR^a)-NR^cR^d$, $-NR^a-C(=NR^a)-R^a$, $-NR^a-NR^a-C(=NR^a)-NR^cR^d$, $-C(H)=N-NR^a-C(=NR^a)-NR^cR^d$, $-C(=O)-NR^a-C(=NR^a)-NR^cR^d$, $-C(=O)-NR^a-C(=NR^a)-R^a$, or $R^b$;

$R^3$ is $(C_1-C_6)$alkyl;

each $R^4$ is independently phenyl that is substituted with one or more $R^2$ or $-C(=O)NR^mR^n$ and that is also optionally substituted with one or more halo, $(C_1-C_6)$alkyl, $(C_3-C_6)$cycloalkyl, $(C_1-C_6)$alkoxycarbonyl, or phenyl that is optionally substituted with one or more halo, $(C_1-C_6)$alkyl, or $(C_3-C_6)$cycloalkyl;

each $R^a$ is independently H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl;

each $R^b$ is independently selected from imidazoyl, piperazinyl, triazole, and piperazinyl that is optionally substituted with $(C_1-C_6)$alkyl;

each $R^c$ and $R^d$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$alkyl and heteroaryl$(C_1-C_6)$alkyl wherein any $(C_1-C_6)$alkyl of $R^c$ and $R^d$ is optionally substituted with one or more hydroxy or amino; or $R^c$ and $R^d$ together with the nitrogen to which they are attached form a aziridino, azetidino, morpholino, piperazino, pyrrolidino or piperidino;

each $R^e$ and $R^f$ is independently selected from H, $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$alkyl and heteroaryl$(C_1-C_6)$ alkyl wherein any $(C_1-C_6)$alkyl is optionally substituted with one or more hydroxy or amino; or $R^e$ and $R^f$ together with the nitrogen to which they are attached form a aziridino, azetidino, morpholino, piperazino, pyrrolidino or piperidino;

each $R^m$ and $R^n$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$alkyl and heteroaryl$(C_1-C_6)$alkyl wherein any $(C_1-C_6)$alkyl of $R^m$ and $R^n$ is optionally substituted with one or more amino; or $R^m$ and $R^n$ together with the nitrogen to which they are attached form a aziridino, azetidino, morpholino, piperazino, pyrrolidino or piperidino; and each $Z^-$ is independently a suitable counter ion;
or a pharmaceutically acceptable salt thereof.

The invention also provides a novel compound of formula I or a salt thereof.

The invention also provides a composition comprising a compound of formula I, or a pharmaceutically acceptable salt thereof, and a pharmaceutically acceptable vehicle.

The invention also provides a compound of formula I or a pharmaceutically acceptable salt thereof for the prophylactic or therapeutic treatment of a bacterial infection.

The invention also provides a compound of formula I or a pharmaceutically acceptable salt thereof for use in medical treatment.

The invention also provides the use of a compound of formula I or a pharmaceutically acceptable salt thereof for the preparation of a medicament for treating a bacterial infection in a mammal.

The invention also provides processes and intermediates disclosed herein that are useful for preparing compounds of formula I or salts thereof.

DETAILED DESCRIPTION

The following definitions are used, unless otherwise described: halo is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to). In one embodiment alkyl is a $(C_1-C_6)$alkyl and alkoxy is a $(C_1-C_6)$alkoxy. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(Q) wherein Q is absent or is H, O, $(C_1-C_4)$alkyl, phenyl or benzyl; as well as a radical of an ortho-fused bicyclic heterocycle of about eight to ten ring atoms comprising one to four heteroatoms each selected from the group consisting of non-peroxide oxygen, sulfur, and N(Q).

As used herein "cycloalkyl" refers to a saturated or partially unsaturated cyclic hydrocarbon ring system. In one embodiment "cycloalkyl" includes $(C_3-C_6)$cycloalkyl which can be cyclopropyl, cyclobutyl, cyclopentyl, or cyclohexyl.

When the bicyclic heteroaryl ring in formula I is substituted on a ring carbon with $R^1$, $R^2$, or $R^4$ as defined herein it should be understood that the hydrogen atom of the corresponding $X_1$ to $X_8CH$ group is removed and replaced with the $R^1$, $R^2$, or $R^4$ group.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, stereoisomeric, or polymorphic form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

It will also be appreciated by those skilled in the art that certain compounds of the invention can exist in more than one tautomeric form. For example, a substituent of formula —NH—C(=NH)—NH$_2$ in a compound of formula (I) could exist in tautomeric form as —N=C(NH$_2$)—NH$_2$, or a substituent of formula —NH—C(=NH)—CH$_3$ in a compound of formula (I) could exist in tautomeric form as —N=C(NH$_2$)—CH$_3$. The present invention encompasses all tautomeric forms of a compound of formula I as well as mixtures thereof that can exist in equilibrium with non-charged entities depending upon pH, which possess the useful properties described herein.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; aryl can be phenyl, indenyl, or naphthoyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, benzimidazole, isoquinolyl (or its N-oxide) or quinolyl (or its N-oxide).

As used herein the term "aryl$(C_1-C_6)$alkyl" refers to a $(C_1-C_6)$alkyl radical in which one or more of the hydrogen atoms of the $(C_1-C_6)$alkyl radical is replaced with an aryl radical. As used herein the term "heteroaryl$(C_1-C_6)$ alkyl" refers to a $(C_1-C_6)$alkyl radical in which one or more of the hydrogen atoms of the $(C_1-C_6)$alkyl radical is replaced with a heteroaryl radical. As used herein the term "$(C_3-C_6)$ cycloalkyl$C_1-C_6$)alkyl" refers to a $(C_1-C_6)$alkyl radical in which one or more of the hydrogen atoms of the $(C_1-C_6)$ alkyl radical is replaced with a $(C_3-C_6)$cycloalkylradical.

In one embodiment of the invention the compound of formula I is a bicyclic ring selected from:

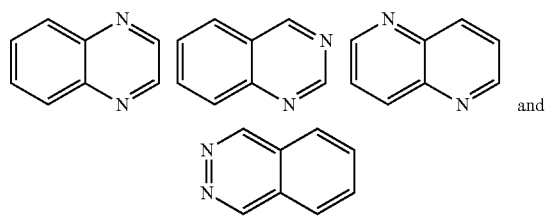

and wherein the bicyclic ring is a) substituted on a first ring carbon with a group $R^1$ and substituted on a second ring carbon with a group $R^2$; or is b) substituted on a ring carbon with a group $R^1$ and substituted on a ring nitrogen with $R^3$ to form the corresponding ammonium salt that has a suitable counter ion $X^-$; or is c) substituted on a ring carbon with a group $R^4$.

In one embodiment of the invention the compound of formula I is a bicyclic ring of formula:

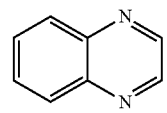

that is a) substituted on a first ring carbon with a group $R^1$ and substituted on a second ring carbon with a group $R^2$; or is b) substituted on a ring carbon with a group $R^1$ and substituted on a ring nitrogen with $R^3$ to form the corresponding ammonium salt that has a suitable counter ion $X^-$; or is c) substituted on a ring carbon with a group $R^4$.

In one embodiment of the invention the compound of formula I is a bicyclic ring of formula:

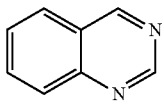

that is a) substituted on a first ring carbon with a group $R^1$ and substituted on a second ring carbon with a group $R^2$; or is b) substituted on a ring carbon with a group $R^1$ and substituted on a ring nitrogen with $R^3$ to form the corresponding ammonium salt that has a suitable counter ion $X^-$; or is c) substituted on a ring carbon with a group $R^4$.

In one embodiment of the invention the compound of formula I is a bicyclic ring of formula:

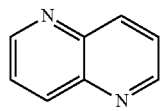

that is a) substituted on a first ring carbon with a group $R^1$ and substituted on a second ring carbon with a group $R^2$; or is b) substituted on a ring carbon with a group $R^1$ and substituted on a ring nitrogen with $R^3$ to form the corresponding ammonium salt that has a suitable counter ion $X^-$; or is c) substituted on a ring carbon with a group $R^4$.

In one embodiment of the invention the compound of formula I is a bicyclic ring of formula:

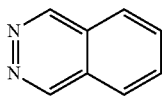

that is a) substituted on a first ring carbon with a group $R^1$ and substituted on a second ring carbon with a group $R^2$; or is b) substituted on a ring carbon with a group $R^1$ and substituted on a ring nitrogen with $R^3$ to form the corresponding ammonium salt that has a suitable counter ion $X^-$; or is c) substituted on a ring carbon with a group $R^4$.

In one embodiment of the invention the compound of formula I is selected from:

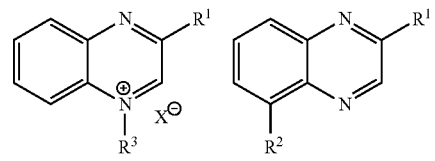

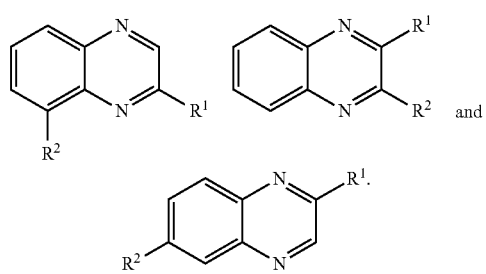

In one embodiment of the invention the compound of formula I is has a formula selected from:

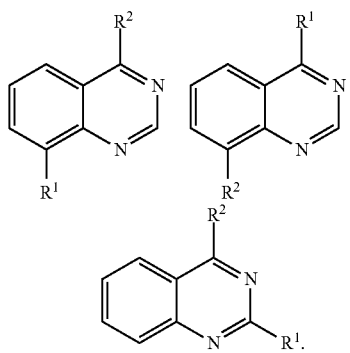

and

In one embodiment of the invention the compound of formula I has the following formula:

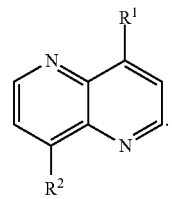

In one embodiment of the invention the compound of formula I is has the following formula:

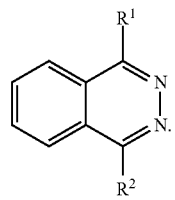

In one embodiment of the invention $R^1$ is phenyl, 3-biphenyl, 3-tert-butylphenyl, 4-tert-butylphenyl, 3-fluorophenyl, 3-methoxycarbonyl-5-(4-tert-butylphenyl)phenyl, 3-aminocarbonyl-5-(4-tert-butylphenyl)phenyl, 3-(N-(2-hydroxyethyl)aminocarbonyl)-5-(4-tert-butylphenyl)phenyl, or 3-methylphenyl.

In one embodiment of the invention $R^2$ is guanadinomethyl, aminomethyl, N-(2-aminoethyl)amino, or —$CH_2$—NH—C(=NH)$CH_3$.

In one embodiment of the invention $R^3$ is methyl and $X^-$ is $I^-$.

In one embodiment of the invention the compound of formula I is has the following formula:

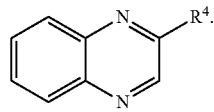

In one embodiment of the invention $R^4$ is 3-(N-(2-aminoethyl)aminocarbonyl)-5-(4-tert-butylphenyl)phenyl.

In one embodiment the invention provides a compound selected from compounds 1-22 and salts thereof.

In one embodiment the compound of the invention is not compound 10 or compound 20 or a salt thereof.

In one embodiment the invention provides a compound selected from compounds of formula I and salts thereof having a minimal inhibitory concentration against MSSA of less than about 16 μm (see Test C below).

In one embodiment the invention provides a compound selected from compounds of formula I and salts thereof having a minimal inhibitory concentration against MSSA of less than about 8 μm.

In one embodiment the invention provides a compound selected from compounds of formula I and salts thereof having a minimal inhibitory concentration against MSSA of less than about 4 μm.

In one embodiment the invention provides a compound selected from compounds of formula I and salts thereof having a minimal inhibitory concentration against MSSA of less than about 2 μm.

Generally, compounds of formula I as well as synthetic intermediates that can be used for preparing compounds of formula I, can be prepared as illustrated in the following Schemes. It is understood that variable groups shown in the Schemes below (e.g. $R_1$, $R_2$, $R_3$, $Ar_1$, and $Ar_2$) can represent the final corresponding groups present in a compound of formula I or that these groups can represent groups that can be converted to the final corresponding groups present in a compound of formula I at a convenient point in a synthetic sequence. For example, in the Schemes below, the variable groups can contain one or more protecting groups that can be removed at a convenient point in a synthetic sequence to provide the final corresponding groups in the compound of formula I.

Processes for preparing compounds of formula I are provided as further embodiments of the invention and are illustrated by the following procedures in which the meanings of the generic radicals are as given above unless otherwise qualified.

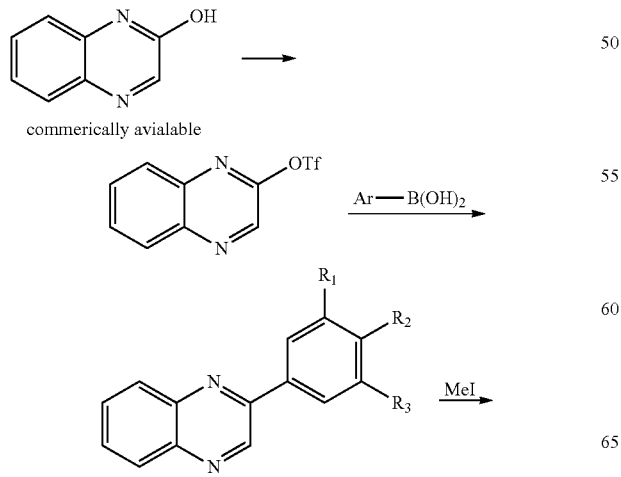

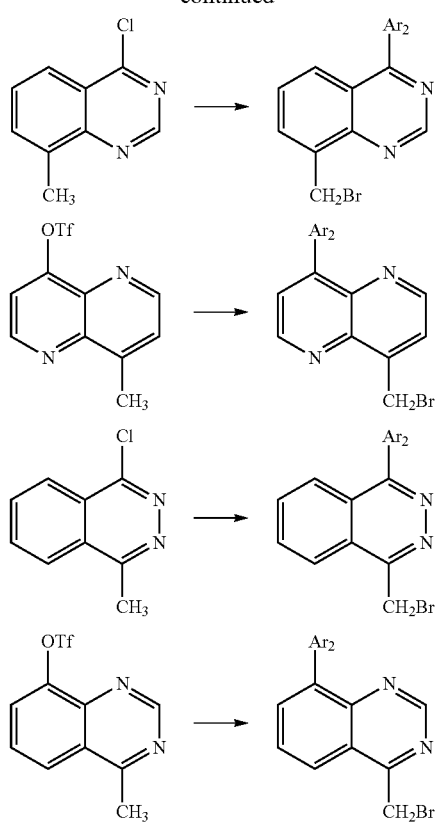
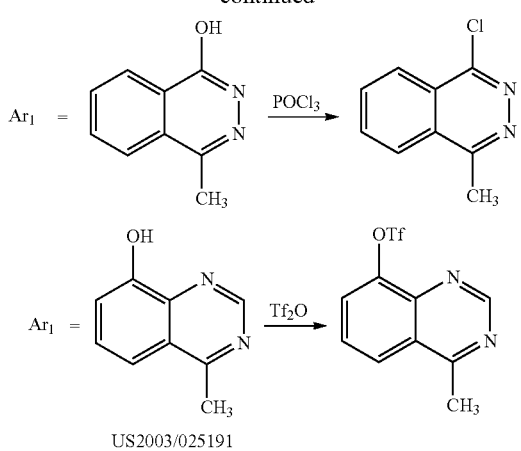
US2003/025191
Scheme 4b. Representative Ar₂ (Aryl) Reactants
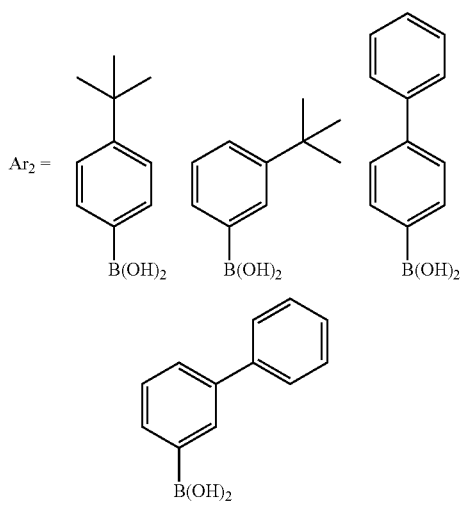
Scheme 4a. Synthesis of Representative Ar₁ (Diazanaphthalene) Intermediates
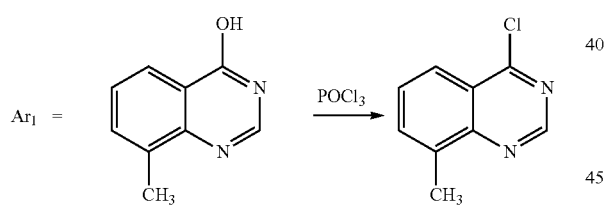
Current Medicinal Chemistry, 11(19), 2549-2553; 2004
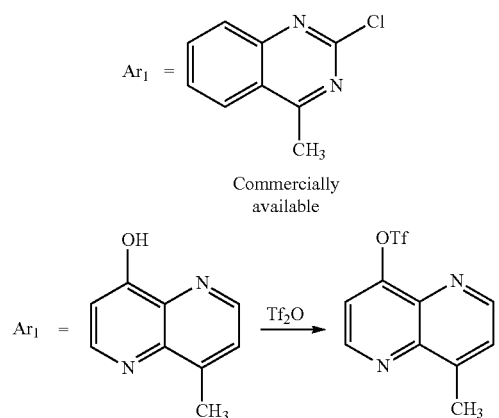
JACS, 2009, 131(2), 763-777
Scheme 5. Functionalized Derivatives Derived from Alkyl Halides of Aryl Substituted Diazanaphthalenes
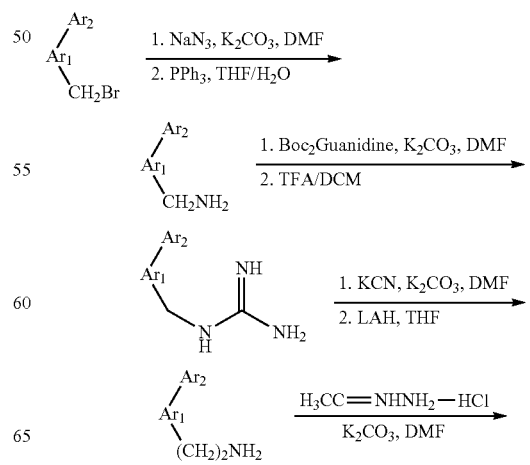

-continued

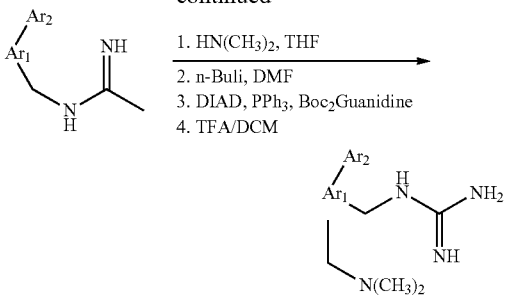

By binding to FtsZ, the compounds of the present invention inhibit the ability of the protein to hydrolyze GTP. This inhibition of FtsZ GTPase activity, in turn, inhibits the ability of the protein to polymerize into Z-rings, as Z-ring formation requires GTP hydrolysis as an energy source for driving the reaction. Since the Z-ring serves as the scaffold for recruitment of all other proteins that comprise the divisome complex, inhibition of Z-ring formation by the compounds of the present invention also results in a corresponding inhibition of divisome protein recruitment.

The compounds of the invention are useful to treat bacterial infections including infections by Gram-negative bacterial strains, Gram-positive bacterial strains and multiple drug-resistant bacterial strains Gram-negative bacterial strains include *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis* and *Haemophilus influenza.*

Gram-positive bacterial strains include *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Bacillus anthracis, Bacillus cereus, Micrococcus luteus, Mycobacterium tuberculosis, Clostridium difficile, Propionibacterium acnes, Streptococcus mutans, Actinomyces viscosus, Actinomyces naeslundii, Streptococcus sanguis, Streptococcus pneumoniae, Streptococcus viridans* and *Streptococcus salivarius.*

Multiple drug-resistant bacterial strains include methicillin-resistant *Staphylococcus aureus*, vancomycin-resistant Enterococci, multiple drug-resistant *Mycobacterium tuberculosis*, and multidrug-resistant *Clostridium difficile.*

In one embodiment compounds of the present invention may be administered as a composition used to treat and/or prevent a bacterial infection wherein the bacterial cell uses polymerized FtsZ protein, or a homolog thereof, to facilitate cytokinesis. To this end, compounds of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, Endocarditis, Prostatitis, Osteomyelitis, Lyme Disease, Pneumonia, or the like.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a fluororquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

The term "prodrug" as used herein refers to any compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself.

By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug resign and Development* (1991), P. Krogsgaard-Larsen and H. Bundgaard, Eds. Harwood Academic Publishers, pp. 113-191; Tranoyl-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases).

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $CF_3SO_3^-$, $p$-$CH_3C_6H_4SO_3^-$, citrate, tartrate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 500 mg/kg, e.g., from about 0.5 to about 400 mg/kg of body weight per day, such as 1 to about 250 mg per kilogram body weight of the recipient per day.

The compound is conveniently formulated in unit dosage form; for example, containing 0.5 to 500 mg, 1 to 400 mg, or 0.5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The impact of a compound of the invention on the dynamics of bacterial FtsZ polymerization can be determined using a method like Test A described below.

Test A. FtsZ Polymerization Assay.

Compound-induced alteration in the dynamics of FtsZ polymerization can be tested using a turbidity assay with purified FtsZ protein. Upon addition of GTP, FtsZ self-associates to form polymeric structures that scatter light at 340 nm to a greater extent than the monomeric protein. The impact of the compounds of the invention on the polymerization dynamics of FtsZ can be detected by an increase or decrease in the extent of GTP-induced light scattering (as determined by corresponding changes in optical density at 340 nm) relative to that observed in the absence of compound. Quantitation of the overall extent of light scattering as a function of compound concentration provides an indication of the potency of that compound at altering the dynamics of FtsZ polymerization.

The impact of a compound of the invention on FtsZ Z-ring formation in bacteria can be determined using a method like Test B described below.

Test B. FtsZ Z-Ring Assay.

The impact of a compound on FtsZ Z-ring formation can be determined using a strain of Bacillus subtilis (FG347) that expresses a green fluorescent protein (GFP)-ZapA fusion protein upon induction with xylose. ZapA is known to associate with FtsZ Z-rings in B. subtilis and, thus, serves as a marker for Z-ring formation. In this assay, log-phase FG347 bacteria are treated with differing concentrations of compound for time periods ranging from 1 to 6 hours. At each time point, aliquots are taken from each culture and then viewed with a fluorescence microscope. In the absence of compound, the bacteria exhibit green fluorescent foci (Z-rings) localized at mid-cell. By contrast, bacteria treated with a compound that disrupts Z-ring formation do not exhibit the green fluorescent Z-rings at mid-cell and are typically associated with an elongated, filamentous phenotype.

The antibacterial activity of a compound of the invention can be determined using a method like Test C described below.

Test C. Antibacterial Assay.

Antibacterial activity can be determined as per Clinical and Laboratory Standards Institute (CLSI) guidelines using a broth microdilution assay in which log-phase bacteria are grown at 37° C. in appropriate medium containing two-fold serial dilutions of a compound to yield final concentrations ranging from 256 to 0.06 µg/mL. For determination of minimal inhibitory concentration (MIC) values, bacterial growth is monitored after 24 to 48 hours by measuring optical density at 600 nm. MIC values reflect the minimal compound concentrations at which bacterial growth is completely inhibited.

Using a procedure similar to Test C, representative compounds of the invention were tested against methicillin-susceptible Staphylococcus aureus (MSSA) and methicillin-resistant Staphylococcus aureus (MRSA). Results are shown in Table 1.

TABLE 1

Minimal Inhibitory Concentrations against MSSA and MRSA for representative compounds of the Invention

| Example # | STRUCTURE | MSSA (MIC ug/ml) | MRSA (MIC ug/ml)* |
|---|---|---|---|
| Example 1 | 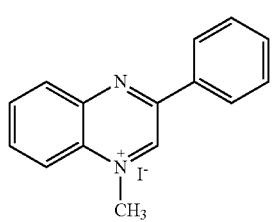 | 2.0 | 8.0 |

TABLE 1-continued
Minimal Inhibitory Concentrations against MSSA and MRSA for representative compounds of the Invention
| Example # | STRUCTURE | MSSA (MIC ug/ml) | MRSA (MIC ug/ml)* |
|---|---|---|---|
| Example 2 | 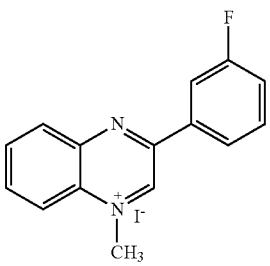 | 2.0 | 4.0 |
| Example 3 | 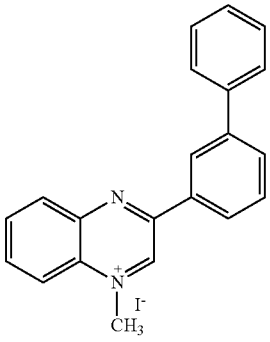 | 0.25 | 0.25 |
| Example 4 | 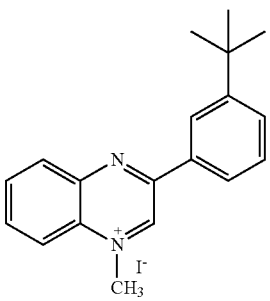 | 0.5 | 1.0 |
| Example 5 | 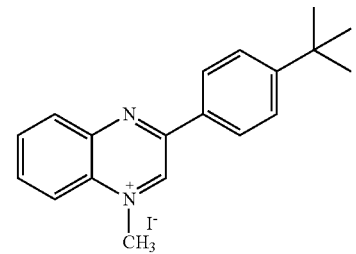 | 0.5 | 1.0 |

TABLE 1-continued

Minimal Inhibitory Concentrations against MSSA and MRSA for representative compounds of the Invention

| Example # | STRUCTURE | MSSA (MIC ug/ml) | MRSA (MIC ug/ml)* |
|---|---|---|---|
| Example 6 | (structure: 4-tert-butylphenyl-phenyl-CO₂Me substituted N-methyl quinoxalinium iodide) | 0.5 | 1.0 |
| Example 7 | (structure: 4-tert-butylphenyl-phenyl-C(O)NH₂ substituted N-methyl quinoxalinium iodide) | 2.0 | 2.0 |
| Example 8 | (structure: 4-tert-butylphenyl-phenyl-C(O)NH-CH₂CH₂-OH substituted N-methyl quinoxalinium iodide) | 4.0 | 4.0 |

TABLE 1-continued
Minimal Inhibitory Concentrations against MSSA and MRSA for representative compounds of the Invention
| Example # | STRUCTURE | MSSA (MIC ug/ml) | MRSA (MIC ug/ml)* |
|---|---|---|---|
| Example 9 | 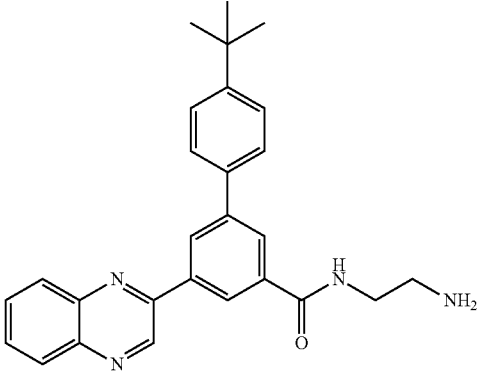 [SMILES: CC(C)(C)c1ccc(-c2cc(C(=O)NCCN)cc(-c3cnc4ccccc4n3)c2)cc1] | 4.0 | 4.0 |
| Example 10 | 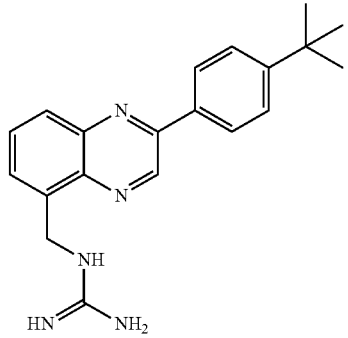 [SMILES: CC(C)(C)c1ccc(-c2cnc3c(CNC(=N)N)cccc3n2)cc1] | 2.0 | 2.0 |
| Example 11 | 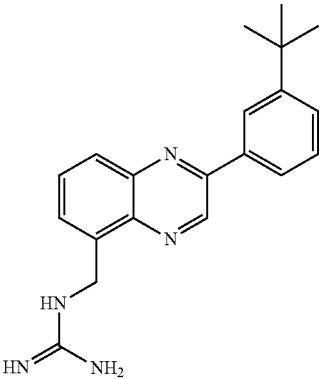 [SMILES: CC(C)(C)c1cccc(-c2cnc3c(CNC(=N)N)cccc3n2)c1] | 1.0 | 2.0 |

TABLE 1-continued
Minimal Inhibitory Concentrations against MSSA and MRSA for representative compounds of the Invention
| Example # | STRUCTURE | MSSA (MIC ug/ml) | MRSA (MIC ug/ml)* |
|---|---|---|---|
| Example 12 | 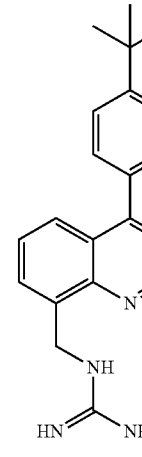 | 2.0 | 4.0 |
| Example 13 | 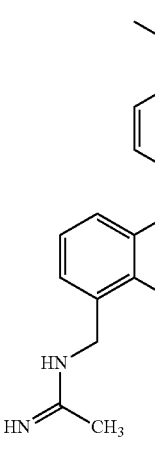 | 32 | 64 |
| Example 14 | 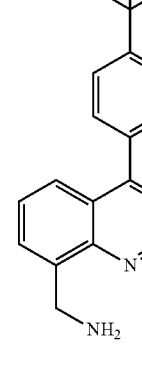 | 32 | 64 |
| Example 15 | 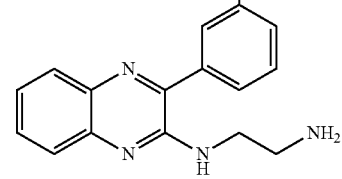 | >64 | >64 |

TABLE 1-continued
Minimal Inhibitory Concentrations against MSSA and MRSA for representative compounds of the Invention
| Example # | STRUCTURE | MSSA (MIC ug/ml) | MRSA (MIC ug/ml)* |
|---|---|---|---|
| Example 16 | 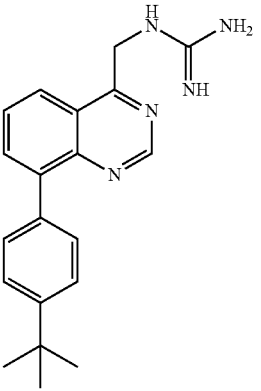 [SMILES: CC(C)(C)c1ccc(-c2cccc3c(CNC(=N)N)ncnc23)cc1] | 8.0 | 64 |
| Example 17 | 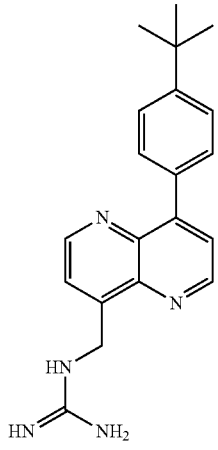 [SMILES: CC(C)(C)c1ccc(-c2ccnc3c(CNC(=N)N)ccnc23)cc1] | 4.0 | 8.0 |
| Example 18 | 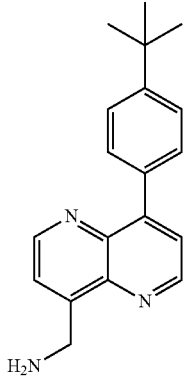 [SMILES: CC(C)(C)c1ccc(-c2ccnc3c(CN)ccnc23)cc1] | >64 | >64 |

TABLE 1-continued

Minimal Inhibitory Concentrations against MSSA and MRSA for representative compounds of the Invention

| Example # | STRUCTURE | MSSA (MIC ug/ml) | MRSA (MIC ug/ml)* |
|---|---|---|---|
| Example 19 | (4-tert-butylphenyl phthalazine with CH2-guanidine) | 16 | n/d |
| Example 20 | (2-(3-tert-butylphenyl)quinazoline with CH2-guanidine at 4-position) | 4.0 | n/d |
| Example 21 | (3-(3-tert-butylphenyl)quinoxaline with CH2-guanidine at 8-position) | 2.0 | 2.0 |
| Example 22 | (2-(3-tert-butylphenyl)quinoxaline with CH2-guanidine at 6-position) | 4.0 | 8.0 |

*n/d = not determined

Representative compounds of the invention were also tested against vancomycin-resistant *Enterococcus faecalis* and *Enterococcus faecium* (VRE), vancomycin-sensitive *Enterococcus faecalis* and *Enterococcus faecium* (VSE). *Streptococcus pyogenes*, *Streptococcus agalactiae*, *Clostridium difficile*, *Propionibacterium acnes*, *Bacillus subtilis*, and *Escherichia coli*, and they were found to have significant antibacterial activity.

The invention will now be illustrated by the following non-limiting Examples.

EXAMPLES

General Methods

Column chromatography refers to flash chromatography conducted on disposable normal phase Teledyne ISCO column using CombiFlash Rf Teledyne ISCO using the solvent systems indicated. Proton ($^1$H NMR) and carbon ($^{13}$C NMR) nuclear magnetic resonance were recorded using either Bruker 400 MHz or Varian 300 MHz Unity Inova spectrometer in the deuterated solvent indicated with chemical shifts reported in δ units downfield from tetramethylsilane (TMS). Coupling constants are reported in hertz (Hz). Starting materials and reagents were purchased from Aldrich. Solvents were purchased from Fisher Scientific, and were A.C.S. grade or HPLC grade. Methylene chloride was freshly distilled from calcium hydride. All other solvents were used as provided without further purification.

Example 1

Preparation of Compound 1

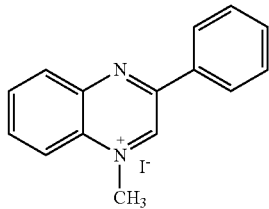

A solution of 2-phenylquinoxaline 1a (75 mg, 0.363 mmol) in iodomethane (2.5 mL) in a sealed vial was stirred at 80° C. overnight. After cooled to room temperature, Et$_2$O was added to the suspension. The solid was collected by filtration to afford the desired compound (61 mg, 48%) as a red solid. $^1$H NMR (DMSO-d$_6$, 300 MHz) δ 10.29 (s, 1H), 8.62-8.53 (m, 2H), 8.43-8.40 (m, 2H), 8.31-8.28 (m, 2H), 7.75-7.72 (m, 3H), 4.79 (s, 3H).

The requisite intermediate was prepared as follows:
a. Preparation of Compound 1a

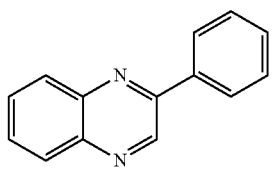 [SMILES: c1ccc(-c2cnc3ccccc3n2)cc1]

A microwave tube equipped with a magnetic stirrer, was charged with quinoxalin-2-yl trifluoromethanesulfonate (128 mg, 0.46 mmol), phenylboronic acid (150 mg, 1.23 mmol), dioxane (3.0 ml), Cs$_2$CO$_3$ (500 mg) and Pd(PPh$_3$)$_2$Cl$_2$ (30 mg). The resulting solution was irradiated for 15 min. After cooled to room temperature, the reaction mixture was diluted with EtOAc and washed with saturated NaHCO$_3$, dried over Na$_2$SO$_4$. The organic layer was concentrated under reduced pressure and purified on silica gel. Elution with EtOAc/hexanes solvent system afforded the desired compound as a white solid (88 mg, 92% yield). $^1$H NMR (CDCl$_3$, 400 MHz) δ 9.26 (s, 1H), 8.14-8.04 (m, 4H), 7.73-7.66 (m, 2H), 7.55-7.44 (m, 3H).

Example 2

Preparation of Compound 2

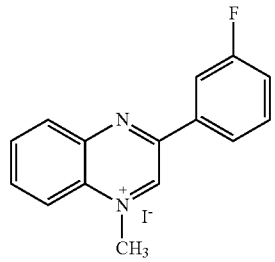

A solution of 2-(3-fluorophenyl)quioxaline 2a (30 mg, 0.08 mmol) in iodomethane (1.0 mL) in a sealed 2-dram vial was stirred at 80° C. overnight. After cooled to room temperature, Et$_2$O was added to the suspension. The solid was collected by filtration to afford the desired compound (35 mg, 85%) as an orange solid. $^1$H NMR (300 MHz, DMSO-d$_6$) δ 10.33 (s, 1H), 8.64-8.54 (m, 2H), 8.35-8.21 (m, 4H), 7.83-7.76 (m, 1H), 7.62-7.57 (m, 1H), 4.78 (s, 3H).

The requisite intermediate was prepared as follows:
a. Preparation of Compound 2a

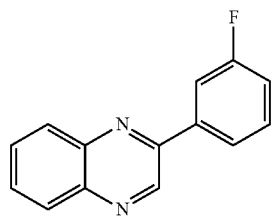 [SMILES: Fc1cccc(-c2cnc3ccccc3n2)c1]

A 25-mL round bottom flask equipped with a magnetic stirrer, a condenser and a nitrogen in/outlet adapter was charged with 2-bromoquinoxaline (100 mg, 0.48 mmol), 4-Fluorophenylboronic acid (80 mg, 0.57 mmol), water/dioxane (1.0 mL/4.0 ml), K$_2$CO$_3$ (132 mg, 0.96 mmol). The resulting solution was degassed for 15 min, then Pd(PPh$_3$)$_4$ (27 mg, 0.024 mmol) was added. The reaction mixture was warmed to 100° C. and stirred for 1 h. After cooled to room temperature, the reaction mixture was diluted with EtOAc and washed with saturated NaHCO$_3$, brine, dried over Na$_2$SO$_4$. The organic layer was concentrated under reduced pressure and purified on silica gel. Elution with EtOAc/hexanes solvent system afforded the desired compound (40 mg, 38% yield). $^1$H NMR (400 MHz, CDCl$_3$) δ 9.34 (s, 1H), 8.18 (m, 2H), 8.00 (m, 2H), 7.82 (m, 2H), 7.57 (m, 1H), 7.25 (m, 1H).

Example 3

Preparation of Compound 3

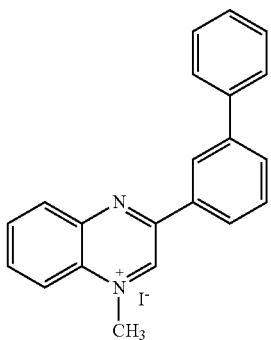

A solution of the 2-([1,1'-biphenyl]-3-yl)quinoxaline 3a (100 mg, 0.354 mmol) in iodomethane (3.0 mL) in a sealed vial was stirred at 80° C. overnight. After cooled to room temperature, Et$_2$O was added to the suspension. The solid was collected by filtration to afford the desired compound (81 mg, 54%) as an orange solid. $^1$H NMR (300 MHz, CD$_3$OD) δ 10.21 (s, 1H), 8.58 (s, 1H), 8.52-8.49 (m, 2H), 8.32 (d, J=8.0 Hz, 1H), 8.20 (m, 2H), 7.87 (d, J=6.0 Hz, 1H), 7.71-7.66 (m, 3H), 7.44 (m, 2H), 7.36 (m, 1H), 4.85 (s, 3H).

The requisite intermediate was prepared as follows:

a. Preparation of Compound 3a

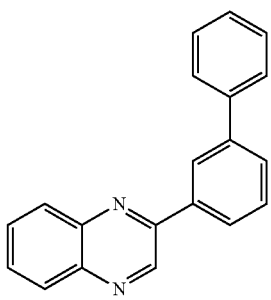 [SMILES: c1ccc(-c2cccc(-c3cnc4ccccc4n3)c2)cc1]

A microwave tube equipped with a magnetic stirrer, was charged with quinoxalin-2-yl trifluoromethanesulfonate (175 mg, 0.63 mmol), 3-biphenylboronic acid (200 mg, 1.0 mmol), dioxane (3.0 ml), Cs$_2$CO$_3$ (500 mg) and Pd(PPh$_3$)$_2$Cl$_2$ (30 mg). The resulting solution was irradiated at 120° C. for 15 min. After cooled to room temperature, the reaction mixture was diluted with EtOAc and washed with saturated NaHCO$_3$, dried over Na$_2$SO$_4$. The organic layer was concentrated under reduced pressure and purified on silica gel. Elution with EtOAc/hexanes solvent system afforded the desired compound as a white solid (150 mg, 85% yield). $^1$H NMR (400 MHz, CDCl$_3$) δ 9.39 (s, 1H), 8.43 (s, 1H), 8.20-8.13 (m, 3H), 7.81-7.70 (m, 4H), 7.65 (t, J=4.0 Hz, 2H), 7.50 (t, J=4.0 Hz, 2H), 7.39 (t, J=4.0 Hz, 1H).

Example 4

Preparation of Compound 4

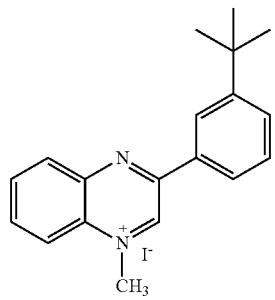

A solution of the 2-(3-(tert-butyl)phenyl)quinoxaline 4a (70 mg, 0.267 mmol) in iodomethane (2.0 mL) in a sealed vial was stirred at 80° C. overnight. After cooled to room temperature, Et$_2$O was added to the suspension. The solid was collected by filtration to afford the desired compound (52 mg, 48%) as yellow solid. $^1$H NMR (300 MHz, DMSO-d$_6$) δ 10.27 (s, 1H), 8.63-8.54 (m, 2H), 8.40 (s, 1H), 8.31-8.27 (m, 2H), 8.23 (d, J=8.0 Hz, 1H), 7.76 (m, 1H), 7.66 (m, 1H), 4.80 (s, 3H), 1.43 (s, 9H).

The requisite intermediate was prepared as follows:

a. Preparation of Compound 4a

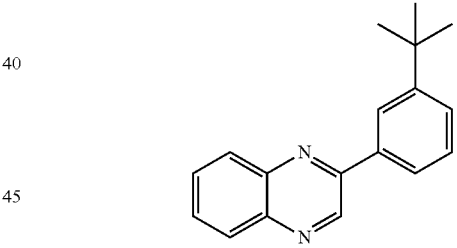

A microwave tube equipped with a magnetic stirrer, was charged with quinoxalin-2-yl trifluoromethanesulfonate (165 mg, 0.59 mmol), 3-tert-butylphenylboronic acid (200 mg, 1.12 mmol), dioxane (3.0 ml), Cs$_2$CO$_3$ (500 mg) and Pd(PPh$_3$)$_2$Cl$_2$ (30 mg). The resulting solution was irradiated at 120° C. for 15 min. After cooled to room temperature, the reaction mixture was diluted with EtOAc and washed with saturated NaHCO$_3$, dried over Na$_2$SO$_4$. The organic layer was concentrated under reduced pressure and purified on silica gel. Elution with EtOAc/hexanes solvent system afforded the desired compound as a white solid (145 mg, 93% yield). $^1$H NMR (300 MHz, CDCl$_3$) δ 9.32 (s, 1H), 8.23-8.17 (m, 3H), 7.97 (dt, J=7.5 Hz, 1H), 7.82-7.72 (m, 2H), 7.6-7.48 (m, 2H), 1.43 (s, 9H).

Example 5

Preparation of Compound 5

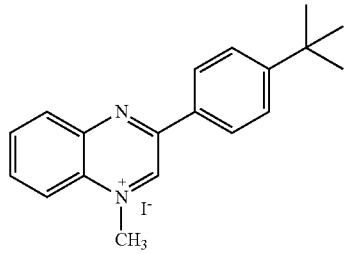

A solution of the 2-(4-(tert-butyl)phenyl)quinoxaline 5a (80 mg, 0.305 mmol) in iodomethane (3.0 mL) in a sealed vial was stirred at 80° C. overnight. After cooled to room temperature, Et$_2$O was added to the suspension. The solid was collected by filtration to afford the desired compound (69 mg, 56%) as a red solid. $^1$H NMR (300 MHz, CD$_3$OD) δ 10.10 (s, 1H), 8.57 (m, 2H), 8.41 (d, J=6.6 Hz, 2H), 8.30-8.27 (m, 2H), 7.76 (d, J=8.4 Hz, 2H), 4.82 (s, 3H), 1.42 (s, 9H).

The requisite intermediate was prepared as follows:
a. Preparation of Compound 5a

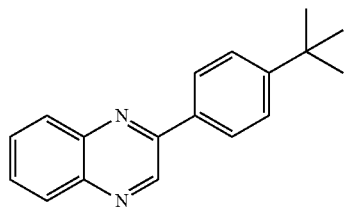 [SMILES: CC(C)(C)c1ccc(-c2cnc3ccccc3n2)cc1]

A microwave tube equipped with a magnetic stirrer, was charged with quinoxalin-2-yl trifluoromethanesulfonate (165 mg, 0.59 mmol), 3-tert-butylphenylboronic acid (200 mg, 1.12 mmol), dioxane (3.0 ml), Cs$_2$CO$_3$ (500 mg) and Pd(PPh$_3$)$_2$Cl$_2$ (30 mg). The resulting solution was irradiated at 120° C. for 15 min. After cooled to room temperature, the reaction mixture was diluted with EtOAc and washed with saturated NaHCO$_3$, dried over Na$_2$SO$_4$. The organic layer was concentrated under reduced pressure and purified on silica gel. Elution with EtOAc/hexanes solvent system afforded the desired compound as a white solid (130 mg, 83% yield). $^1$H NMR (300 MHz, CDCl$_3$) δ 9.32 (s, 1H), 8.12-8.09 (m, 4H), 7.81-7.71 (m, 2H), 7.59 (d, J=6.6 Hz, 2H), 1.39 (s, 9H).

Example 6

Preparation of Compound 6

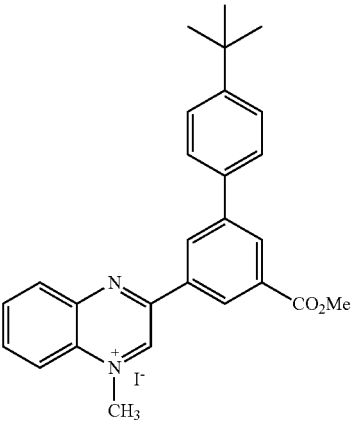

A solution of the substituted ester 6c (15 mg, 0.038 mmol) in iodomethane (1.5 mL) in a sealed 2-dram vial was stirred at 90° C. overnight. After cooled to room temperature, Et$_2$O was added to the suspension. The solid was collected by filtration to afford the desired compound (10 mg, 50%) as a light brown solid. $^1$H NMR (300 MHz, DMSO-d$_6$) δ 10.48 (s, 1H), 8.93 (t, J=1.5 Hz, 1H), 8.88 (t, J=1.6 Hz, 1H), 8.65-8.63 (m, 2H), 8.45 (t, J=1.5 Hz, 1H), 8.35-4.31 (m, 2H), 7.81 (d, J=8.4 Hz, 2H), 7.62 (d, J=8.4 hz, 2H), 4.82 (s, 3H), 3.98 (s, 3H), 1.36 (s, 9H).

The requisite intermediates were prepared as follows:
a. Preparation of Compound 6a

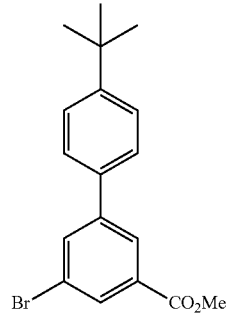 [SMILES: COC(=O)c1cc(Br)cc(-c2ccc(C(C)(C)C)cc2)c1]

A 100-mL round bottom flask equipped with a magnetic stirrer, a condenser and a nitrogen in/outlet adapter was charged with commercially available methyl 3-bromo-5-iodobenzoate (2.83 g, 8.3 mmol), 4-tert-butylphenylboronic acid (1.64 g, 9.2 mmol), water/dioxane (10 mL/30 ml), K$_2$CO$_3$ (2.3 g, 16.6 mmol). The resulting solution was degassed for 15 min, then Pd(PPh$_3$)$_4$ (340 mg) was added. The reaction mixture was warmed to 100° C. and stirred for 3 h. After cooled to room temperature, the reaction mixture was diluted with EtOAc (100 mL) and washed with saturated NaHCO$_3$ (30 mL), brine (30 mL), dried over Na$_2$SO$_4$. The organic layer was concentrated under reduced pressure and purified on silica gel. Elution with EtOAc/hexanes solvent system afforded the desired compound (1.69 g, 58% yield). $^1$H NMR (300 MHz, CDCl$_3$) δ 8.19 (a, 1H), 8.12 (s, 1H), 7.91 (s, 1H), 7.52 (m, 4H), 3.95 (s, 3H), 1.38 (s, 9H).
b. Preparation of Compound 6b

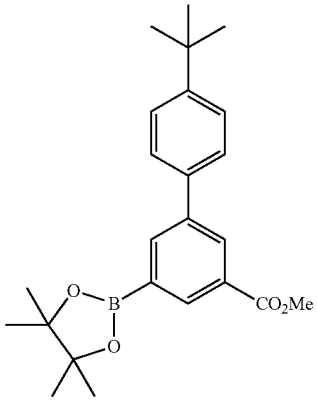 [SMILES: COC(=O)c1cc(B2OC(C)(C)C(C)(C)O2)cc(-c2ccc(C(C)(C)C)cc2)c1]

To a solution of 6a (400 mg, 1.15 mmol), in 5.0 mL dioxane was added KOAc (332 mg, 3.45 mmol), diborane (322 mg, 1.27 mmol) followed by Pd(dppf)Cl$_2$. The mixture was heated at 80° C. for 16 h. The reaction mixture was cooled to room temperature, the solids were filtered off, the solvent was removed and the crude product was purfied in ISCO using 10% EtOAc in hexane to afford the desired product (300 mg, 66% yield). $^1$H NMR (300 MHz, CDCl$_3$) δ 8.42 (s, 1H), 8.37 (s, 1H), 8.22 (s, 1H), 7.61 (d, J=8.7 Hz, 2H), 7.47 (d, J=8.4 Hz, 2H), 3.94 (s, 3H), 1.36 (s, 21H).

c. Preparation of Compound 6c

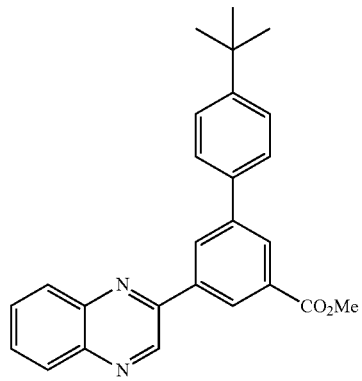 [SMILES: COC(=O)c1cc(-c2ccc(C(C)(C)C)cc2)cc(-c2cnc3ccccc3n2)c1]

A 25-mL round bottom flask equipped with a magnetic stirrer, a condenser and a nitrogen in/outlet adapter was charged with 2-bromoquinoxaline (13 mg, 0.063 mmol), boronate ester 6b (25 mg, 0.063 mmol), water/dioxane (1.0 mL/4.0 ml), $K_2CO_3$ (17 mg, 0.126 mmol). The resulting solution was degassed for 15 min, then $Pd(PPh_3)_4$ (5 mg) was added. The reaction mixture was warmed to 100° C. and stirred for 1 h. After cooled to room temperature, the reaction mixture was diluted with EtOAc and washed with saturated $NaHCO_3$, brine, dried over $Na_2SO_4$. The organic layer was concentrated under reduced pressure and purified on silica gel. Elution with 10% EtOAc/hexanes solvent system afforded the desired compound (15 mg, 60% yield). $^1$H NMR (300 MHz, $CDCl_3$) δ 9.46 (s, 1H), 8.83 (s, 1H), 8.69 (m, 1H), 8.46 (s, 1H), 8.21 (m, 2H), 7.86 (m, 2H), 7.72 (d, J=12.0 Hz, 2H), 7.58 (d, J=12.0 Hz, 2H), 4.05 (s, 3H), 1.42 (s, 9H).

Example 7

Preparation of Compound 7

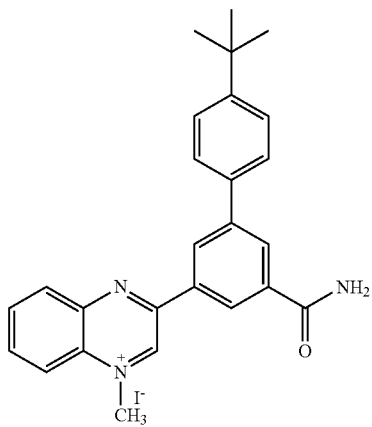

A solution of the amide 7b (12 mg, 0.031 mmol) in iodomethane (1.0 mL) in a sealed 2-dram vial was stirred at 60° C. overnight. After cooled to room temperature, $Et_2O$ was added to the suspension. The solid was collected by filtration to afford the desired compound (14 mg, 85%) as a yellow solid. $^1$H NMR (300 MHz, DMSO-$d_6$) δ 10.44 (s, 1H), 8.89 (s, 1H), 8.72 (s, 1H), 8.46 (s, 1H), 8.32 (m, 4H), 7.85 (d, J=6.6 Hz, 2H), 7.61 (d, J=6.6 Hz, 2H), 4.82 (s, 3H), 1.37 (s, 9H).

The requisite intermediates were prepared as follows:

a. Preparation of Compound 7a

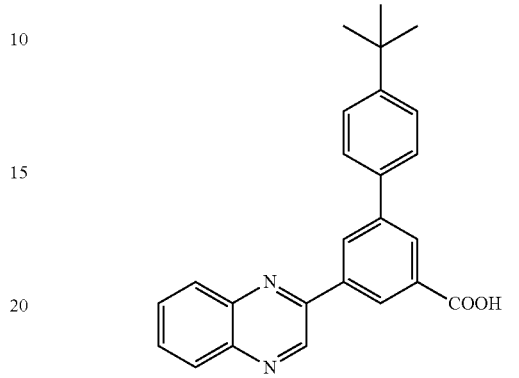

To a solution of the ester 6c (90 mg, 0.23 mmol) in THF:$H_2O$ (4.0 ml:2.0 ml) was added LiOH.$H_2O$ (50 mg) and the mixture was stirred at 50° C. overnight. The organic solvent was removed and the aqueous portion was adjusted to pH2 by addition of 2N HCl. The white solid thus formed was collected by filtration. Air drying of the solid provided the desired product as a white solid (74 mg, 84% yield) which was used for the next step without further purification.

b. Preparation of Compound 7b

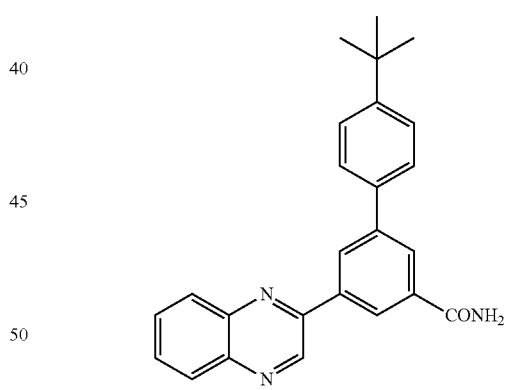

To a suspension of the acid 7a (25 mg, 0.065 mmol) in 2.0 mL of DCM was added 4 drops of oxalyl chloride and one drop of DMF and the mixture was stirred at room temperature. After 1 h, the solvent was removed and the residue was dissolved in DCM. The DCM solution was added to $NH_3$.$H_2O$ (1.0 mL) at 0° C. The mixture was stirred at room temperature for 1 h. The DCM layer was separated and dried over $Na_2SO_4$. The solvent was concentrated and was purified using 70% ethyl acetate in hexane to afford the desired compound as a white solid (12 mg, 48% yield). $^1$H NMR (300 MHz, $CDCl_3$) δ 9.43 (s, 1H), 8.60 (m, 1H), 8.56 (m, 1H), 8.20-8.14 (m, 3H), 7.80 (m, 2H), 7.77 (d, J=6.0 Hz, 2H), 7.54 (d, J=6.0 Hz, 2H), 1.39 (s, 9H).

Example 8

Preparation of Compound 8

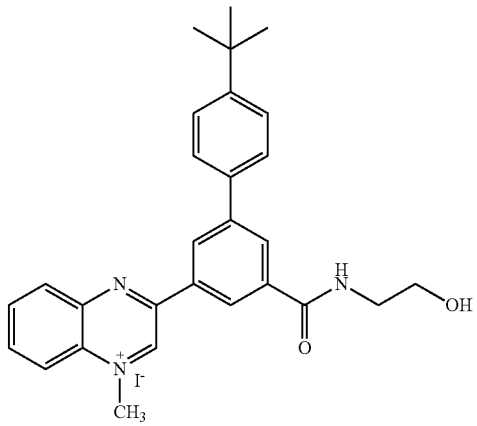

A solution of the amide 8a (15 mg, 0.035 mmol) in iodomethane (1.0 mL) in a sealed 2-dram vial was stirred at 70° C. overnight. After cooled to room temperature, Et$_2$O was added to the suspension. The solid was collected by filtration to afford the desired compound (20 mg, 100%) as a yellow solid. $^1$H NMR (300 MHz, CDCl$_3$) δ 11.26 (s, 1H), 9.04 (s, 1H), 8.74 (s, 1H), 8.48 (m, 1H), 8.31-8.18 (m, 4H), 7.60 (d, J=8.4 Hz, 2H), 7.47 (d, J=8.4 Hz, 2H), 5.08 (s, 3H), 3.84 (m, 2H), 3.56 (m, 2H), 1.38 (s, 9H).

The requisite intermediates were prepared as follows:
a. Preparation of Compound 8a

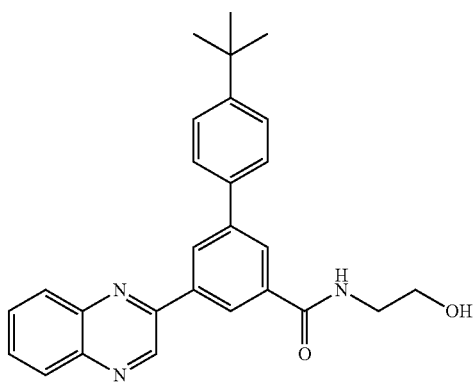 [SMILES: CC(C)(C)c1ccc(-c2cc(C(=O)NCCO)cc(-c3cnc4ccccc4n3)c2)cc1]

To a suspension of the acid 7a (25 mg, 0.065 mmol) in 3.0 mL of DCM was added 4 drops of oxalyl chloride and one drop of DMF and the mixture was stirred at room temperature. After 1 h, the solvent was removed and the residue was dissolved in DCM. The DCM solution was added to ethanolamine (40 mg in 1.0 ml of DCM) and 4 drops of TEA at −78° C. The mixture was gradually warm to room temperature for 1 h. The DCM layer was washed with NaHCO$_3$ and dried over Na$_2$SO$_4$. The solvent was concentrated and was purified using 100% ethyl acetate to afford the desired compound as an orange solid (19 mg, 70% yield). $^1$H NMR (300 MHz, CDCl$_3$) δ 9.30 (s, 1H), 8.44 (d, J=12.0 Hz, 2H), 8.10-8.06 (m, 3H), 7.77-7.70 (m, 2H), 7.56-7.47 (m, 4H), 7.22 (m, 1H), 3.92 (m, 2H), 3.73 (m, 2H), 1.39 (s, 9H).

Example 9

Preparation of Compound 9

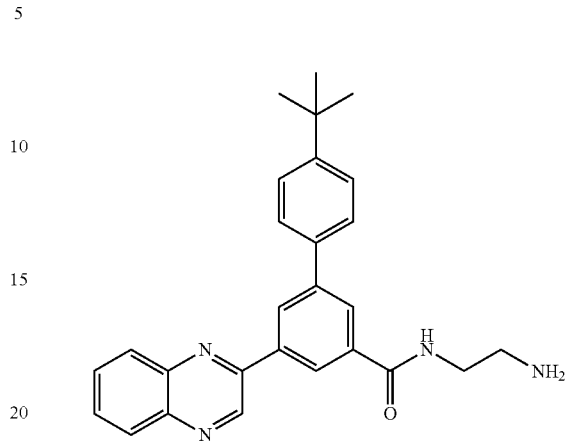

To a suspension of the acid 7a (25 mg, 0.065 mmol) in 3.0 mL of DCM was added 4 drops of oxalyl chloride and one drop of DMF and the mixture was stirred at room temperature. After 1 h, the solvent was removed and the residue was dissolved in DCM. The DCM solution was added to ethylene diamine (25 mg in 1.0 ml of DCM). The mixture was stirred at room temperature for 1 h. The DCM layer was washed with NaHCO$_3$ and dried over Na$_2$SO$_4$. The solvent was concentrated and was purified using 10/89/1:MeOH/CHCl$_3$/ammonium hydroxide to afford the desired compound as a white foam (18 mg, 70% yield). $^1$H NMR (300 MHz, CDCl$_3$) δ 9.41 (s, 1H), 8.54 (d, J=12.0 Hz, 1H), 8.18-8.12 (m, 2H), 7.83-7.74 (m, 2H), 7.76 (d, J=12.0 Hz, 2H), 7.51 (d, J=12.0 Hz, 2H), 7.11 (m, 1H), 3.59 (m, 2H), 3.02 (m, 2H), 1.71 (bs, 3H), 1.32 (s, 9H).

Example 10

Preparation of Compound 10

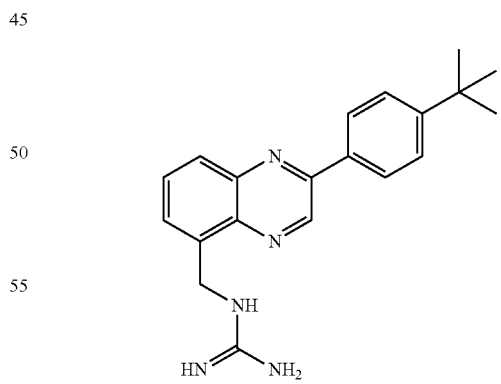

To a 10-mL vial was added di-tert-butyl guanidine compound 10d (20 mg, 0.037 mmol), CH$_2$Cl$_2$ (1.0 mL), and TFA (1.0 mL). The sealed vial was stirred at rt overnight. The solvent was removed and the residue was purified on silica gel. Elution with CH$_2$Cl$_2$ to (10/89/1:MeOH/CHCl$_3$/ammonium hydroxide) afforded the title compound as a white solid (6.5 mg, 53% yield).

The requisite intermediates were prepared as follows:

a. Preparation of Compound 10a

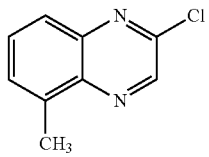

The compound was prepared using a procedure similar to the procedure described by William C. Lumma, Jr., et al., *Journal of Medicinal Chemistry*, 1981, 24(1), 93-101.

b. Preparation of Compound 10b

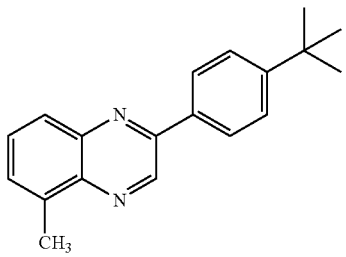 [SMILES: Cc1cccc2nc(-c3ccc(C(C)(C)C)cc3)cnc12]

A microwave tube equipped with a magnetic stirrer, was charged with 2-chloro-5-methylquinoxaline 10a (100 mg, 0.56 mmol), 4-tert-butylphenylboronic acid (150 mg, 0.84 mmol), dioxane (3.0 ml), $Cs_2CO_3$ (400 mg) and $Pd(PPh_3)_2Cl_2$ (30 mg). The resulting solution was irradiated at 120° C. for 15 min. After cooled to room temperature, the reaction mixture was diluted with EtOAc and washed with saturated $NaHCO_3$, dried over $Na_2SO_4$. The organic layer was concentrated under reduced pressure and purified on silica gel. Elution with EtOAc/hexanes solvent system afforded the desired compound as a white solid (80 mg, 52% yield). $^1$H NMR (400 MHz, $CDCl_3$) δ 9.25 (s, 1H), 8.06 (d, J=8.0 Hz, 2H), 7.92 (d, J=8.0 Hz, 1H), 7.59 (t, J=8.0 Hz, 1H), 7.54-7.49 (m, 3H), 2.76 (s, 3H), 1.32 (s, 9H).

c. Preparation of Compound 10c

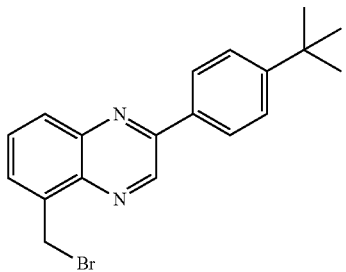 [SMILES: CC(C)(C)c1ccc(-c2cnc3c(CBr)cccc3n2)cc1]

A mixture of substituted quinoxaline 10b (77 mg, 0.28 mmol), NBS (68 mg, 0.385 mmol) in carbon tetrachloride (4.0 mL) was heated under light for 90 minutes. The solids were filtered and the solvent was removed to give the crude product. Purification using 10% ethyl acetate in hexane afforded the product (100 mg, yield) with a mixture with dibrominated product (1:1). The mixture was used for the next step without further separation.

d. Preparation of Compound 10d

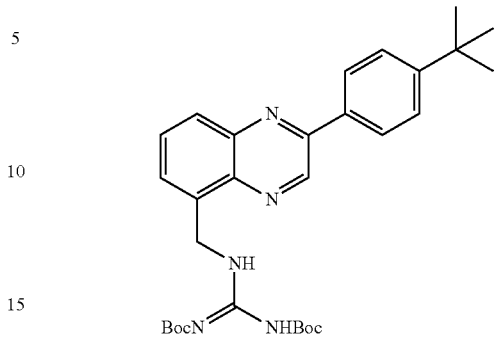

A 25-mL round bottom flask equipped with a magnetic stirrer, a condenser and a nitrogen in/outlet adapter was charged with above mixture 10c (30 mg), DMF (2 mL), $K_2CO_3$ (60 mg, 0.44 mmol), and 1,3-bis(tert-butoxycarbonyl)guanidine (50 mg, 0.19 mmol) The reaction mixture was stirred at 50° C. for 2 h. The reaction mixture was diluted with EtOAc, washed with water, 10% LiCl, brine, dried over $Na_2SO_4$, concentrated, and purified on silica gel. Elution with 20% EtOAc/hexanes afforded the title compound as a white solid (20 mg). $^1$H NMR (400 MHz, $CDCl_3$) δ 9.45 (bs, 2H), 9.23 (s, 1H), 8.08 (d, J=8.4 Hz, 2H), 7.95 (d, J=8.3 Hz, 1H), 7.64 (t, J=7.4 Hz, 1H), 7.53 (d, J=8.4 Hz, 2H), 7.36 (d, J=7.2 Hz, 1H), 5.87 (s, 2H), 1.37 (s, 9H), 1.32 (s, 9H), 1.05 (s, 9H).

Example 11

Preparation of Compound 11

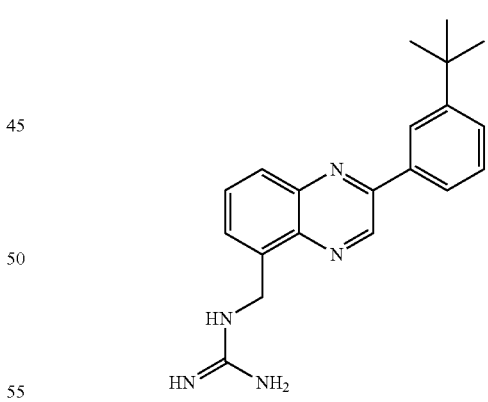

A 10-mL vial was added di-tert-butyl guanidine compound 11c (80 mg, 0.15 mmol), $CH_2Cl_2$ (1.0 mL), and TFA (1.0 mL). The sealed vial was stirred at rt overnight. The solvent was removed and the residue was purified on silica gel. Elution with $CH_2Cl_2$ to (10/89/1:MeOH/$CHCl_3$/ammonium hydroxide) afforded the title compound as white solid (40 mg, 80% yield). $^1$H NMR (300 MHz, $CD_3OD$) δ 9.51 (s, 1H), 8.36 (t, J=1.8 Hz, 1H), 8.19 (dd, J=8.4, 1.8 Hz, 1H), 8.10-8.06 (m, 1H), 7.93-7.82 (m, 2H), 7.69-7.65 (m, 1H), 7.56 (t, J=7.5 hz, 1H), 5.06 (s, 2H), 1.46 (s, 9H).

The requisite intermediates were prepared as follows:
a. Preparation of Compound 11a

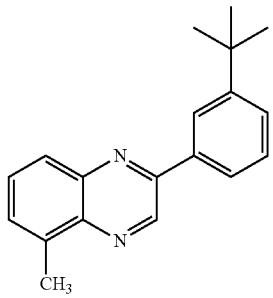 [SMILES: Cc1cccc2nc(-c3cccc(C(C)(C)C)c3)cnc12]

A microwave tube equipped with a magnetic stirrer, was charged with 2-chloro-5-methylquinoxaline 10a (340 mg, 1.90 mmol), 3-tert-butylphenylboronic acid (605 mg, 3.4 mmol), dioxane (3.5 ml), Cs$_2$CO$_3$ (800 mg) and Pd(PPh$_3$)$_2$Cl$_2$ (80 mg). The resulting solution was irradiated at 120° C. for 15 min. After cooled to room temperature, the reaction mixture was diluted with EtOAc and washed with saturated NaHCO$_3$, dried over Na$_2$SO$_4$. The organic layer was concentrated under reduced pressure and purified on silica gel. Elution with EtOAc/hexanes solvent system afforded the desired compound as a white solid (150 mg, 28% yield). $^1$H NMR (300 MHz, CDCl$_3$) δ 9.32 (s, 1H), 8.22 (s, 1H), 8.03-7.95 (m, 2H), 7.67-7.50 (m, 4H), 2.83 (s, 3H), 1.42 (s, 9H).

b. Preparation of Compound 11b

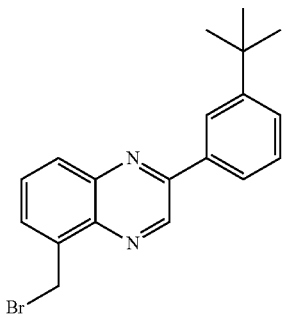 [SMILES: CC(C)(C)c1cccc(-c2cnc3c(CBr)cccc3n2)c1]

A mixture of substituted quinoxaline 11a (120 mg, 0.43 mmol), NBS (116 mg, 0.65 mmol) in carbon tetrachloride (4.0 mL) was heated under light for 60 minutes. The solids were filtered and the solvent was removed to give the crude product. Purification using 10% ethyl acetate in hexane afforded the product (100 mg, 66% yield). NMR (300 MHz, CDCl$_3$) δ: 9.44 (s, 1H), 8.26-8.17 (m, 2H), 8.03-7.75 (m, 4H), 7.61 (m, 2H), 5.25 (s, 2H), 1.46 (s, 9H).

c. Preparation of Compound 11c

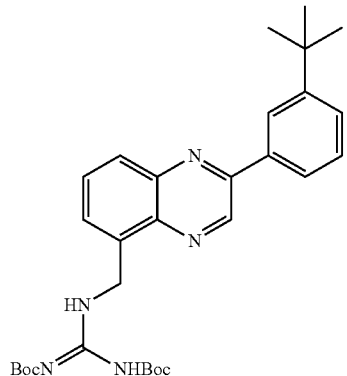

A 25-mL round bottom flask equipped with a magnetic stirrer, a condenser and a nitrogen in/outlet adapter was charged with above bromide 11b (90 mg, 0.254 mmol), DMF (3.0 mL), K$_2$CO$_3$ (70 mg, 0.5 mmol), and 1,3-bis(tert-butoxycarbonyl)guanidine (150 mg, 0.57 mmol) The reaction mixture was stirred at 50° C. for 12 h. The reaction mixture was diluted with EtOAc, washed with water, 10% LiCl, brine, dried over Na$_2$SO$_4$, concentrated, and purified on silica gel. Elution with 10% EtOAc/hexanes afforded the title compound as a white solid (100 mg, 74% yield). $^1$H NMR (CDCl$_3$, 400 MHz) δ 9.5 (bs, 2H), 9.31 (s, 1H), 8.25 (s, 1H), 8.06-7.98 (m, 2H), 7.25 (m, 1H), 7.59-7.43 (m, 3H), 5.94 (s, 2H), 1.44-1.13 (3×9H).

Example 12

Preparation of Compound 12

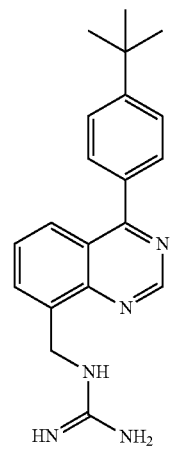 [SMILES: CC(C)(C)c1ccc(-c2ncnc3c(CNC(=N)N)cccc23)cc1]

To a 10-mL vial was added di-tert-butyl guanidine compound 12e (39 mg, 0.073 mmol), CH$_2$Cl$_2$ (1.0 mL), and TFA (1.0 mL). The sealed vial was stirred at rt overnight. The solvent was removed and the residue was purified on silica gel. Elution with CH$_2$Cl$_2$ to (10/89/1:MeOH/CHCl$_3$/ammonium hydroxide) afforded the title compound as white solid (17 mg, 70% yield). $^1$HNMR (400 MHz, CD$_3$OD) δ 9.33 (s, 1H), 8.18 (d, J=8.3 Hz, 1H), 8.02 (d, J=6.8 Hz, 1H), 7.74-7.67 (m, 5H), 5.00 (s, 2H), 1.42 (s, 9H).

The requisite intermediates were prepared as follows:
a. Preparation of Compound 12a

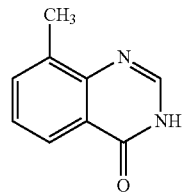

Prepared as described in the literature—European Journal of Medicinal Chemistry, 50, 264-273, 2012.

b. Preparation of Compound 12b

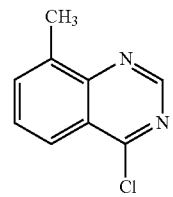

To a solution of 8-methylquinazolin-4(3H)-one 12a (1.1 g, 6.92 mmol) in 155 ml ACN was added 10.1 mL POCl₃. The reaction mixture is refluxed until completion, cooled to room temperature. The solvent was removed under vacuum, and the crude product was purified in ISCO using Ethyl acetate:hexane solvent system to afford the pure product (430 mg, 35% yield). ¹H NMR (CDCl₃, 400 MHz) δ 9.06 (s, 1-H), 8.12 (d, J=8.4 Hz, 1H), 7.80 (d, J=6.9 Hz, 1-H), 7.61 (m, 1H), 2.78 (s, 3H).

c. Preparation of Compound 12c

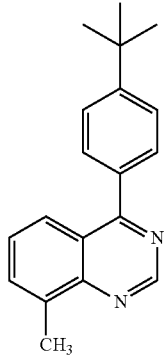 [SMILES: Cc1cccc2c(-c3ccc(C(C)(C)C)cc3)ncnc12]

A 50-mL round bottom flask equipped with a magnetic stirrer, a condenser and a nitrogen in/outlet adapter was charged with 4-chloro-8-methylquinazoline 12b (200 mg, 1.12 mmol), 4-tert-butylphenylboronic acid (300 mg, 1.68 mmol), DME (12 mL), Na₂CO₃ (5.0 ml)(2M). The resulting solution was degassed for 15 min, then Pd(PPh₃)₄ (130 mg, 0.112 mmol) was added. The reaction mixture was warmed to 85° C. and stirred for 1 h. After cooled to room temperature, the reaction mixture was diluted with EtOAc and washed with saturated NaHCO₃, brine, dried over Na₂SO₄. The organic layer was concentrated under reduced pressure and purified on silica gel. Elution with EtOAc/hexanes solvent system afforded the title compound (210 mg, 67% yield). ¹H NMR (CDCl₃, 400 MHz) δ 9.39 (s, 1H), 8.02 (d, J=8.4 Hz, 1H), 7.72 (m, 3H), 7.57 (d, J=8.0 Hz, 2H), 7.54 (m, 1H), 2.83 (s, 3H), 1.39 (s, 9H).

d. Preparation of Compound 12d

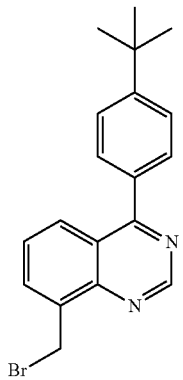 [SMILES: CC(C)(C)c1ccc(-c2ncnc3c(CBr)cccc23)cc1]

A mixture of 4-(4-tert-butyl)phenyl)-8-methylquinazoline 12c (210 mg, 0.76 mmol), NBS (151 mg, 0.84 mmol) in carbon tetrachloride (10.0 mL) was heated under light for 1 h. The solids were filtered and the solvent was removed to give the crude product. Purification using 10% ethyl acetate in hexane afforded the product (163 mg, 60% yield) along with some dibrominated product (40 mg). ¹H NMR (400 MHz, CDCl₃) δ 9.44 (s, 1H), 8.16 (dd, J=8.0, 1.2 Hz, 1H), 8.00 (dd, J=7.2, 1.2 Hz, 1H), 7.70 (m, 3H), 5.20 (s, 2H), 1.39 (s, 9H).

e. Preparation of Compound 12e

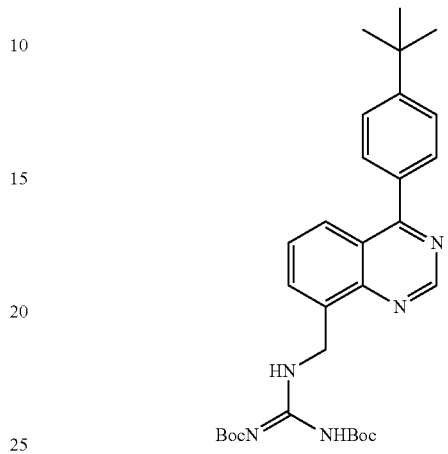

A 10-mL round bottom flask equipped with a magnetic stirrer, a condenser and a nitrogen in/outlet adapter was charged with 8-(bromomethyl)-4-(4-(tert-butyl)phenyl)quinazoline 12d (34 mg, 0.096 mmol), DMF (1.0 mL), K₂CO₃ (27 mg, 0.19 mmol), and 1,3-bis(tert-butoxycarbonyl)guanidine (30 mg, 0.116 mmol) The reaction mixture was stirred at 50° C. for 16 h. The reaction mixture was diluted with EtOAc, washed with water, 10% LiCl, brine, dried over Na₂SO₄, concentrated, and purified on silica gel. Elution with EtOAc/hexanes afforded the title compound as a white solid (39 mg, 76% yield). ¹H NMR (400 MHz, CDCl₃) δ 9.45 (bs, 2H), 9.34 (s, 1H), 8.06 (d, J=7.3 Hz, 1H), 7.73 (d, J=8.0 Hz, 2H), 7.60-7.51 (m, 4H), 5.93 (s, 2H), 1.43 (s, 9H), 1.40 (s, 9H), 1.17 (s, 9H).

Example 13

Preparation of Compound 13

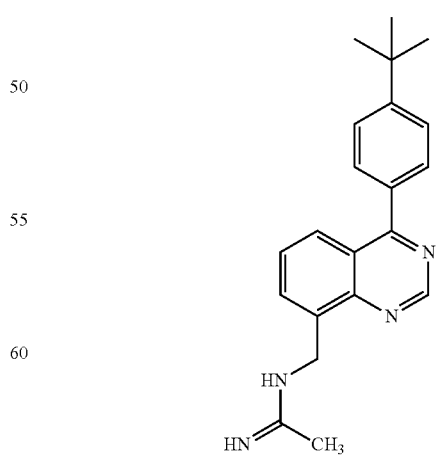

To a mixture of bromide 12d (34.3 mg, 0.096 mmol), K₂CO₃ (27 mg, 0.19 mmol) in 1.0 mL DMF was added acetamidine HCl (11 mg, 0.116 mmol) and the resulting mixture was stirred at room temperature for 16 h. The solvent was removed under vacuum and the resulting residue was purified in ISCO eluting with CH$_2$Cl$_2$ to (10/89/1: MeOH/CHCl$_3$/ammonium hydroxide) which afforded the mono substituted product as white solid (4 mg). $^1$H NMR (400 MHz, CD$_3$OD) δ 9.34 (s, 1H), 8.23 (d, J=8.5 Hz, 1H), 8.05 (d, J=8.0 Hz, 1H), 7.75-7.68 (m, 5H), 5.09 (s, 2H), 2.28 (s, 3H), 1.43 (s, 9H).

Example 14

Preparation of Compound 14

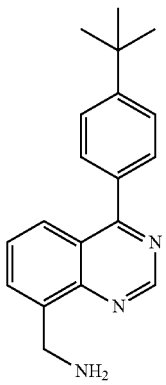

To a solution of azide 14a (23 mg, 0.072 mmol) in 1.8 mL THF and 0.2 mL H$_2$O was added polymer supported PPh$_3$ (116 mg) and the mixture was stirred for 16 h. The solid was filtered off and the solvents were removed under vacuuo. The resulting residue was dissolved in MeOH and was purified in ISCO eluting with CH$_2$Cl$_2$ to (10/89/1:MeOH/CHCl$_3$/ammonium hydroxide) which afforded the title compound as white solid (14 mg, 66% yield). $^1$H NMR (400 MHz, CD$_3$OD) δ 9.29 (s, 1H), 8.09 (dd, J=8.5, 1.2 Hz, 1H), 7.97 (d, J=6.6 Hz, 1H), 7.72-7.64 (m, 5H), 4.42 (s, 2H), 1.42 (s, 9H).

The requisite intermediate was prepared as follows:
a. Preparation of Compound 14a

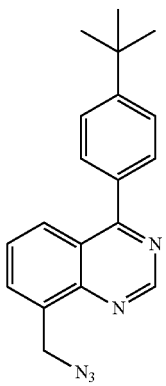 [SMILES: CC(C)(C)c1ccc(-c2ncnc3c(CN=[N+]=[N-])cccc23)cc1]

To a solution of the bromide 12d (25 mg, 0.070 mmol) in 2.5 mL of acetone was added NaN$_3$ (5.5 mg, 0.085 mmol) and the reaction mixture was stirred for 12 h. After the completion of the reaction, the solvent was removed, the residue was diluted with ethyl acetate and was washed with NaHCO$_3$ and brine. Separation in ISCO using Ethyl acetate provided the product (21 mg, 94% yield). $^1$H NMR (400 MHz, CDCl$_3$) δ 9.39 (s, 1H), 8.17 (dd, J=8.5, 1.2 Hz, 1H), 7.92 (d, J=7.0 Hz, 1H), 7.72 (d, J=8.4 Hz, 2H), 7.61-7.58 (m, 3H), 5.06 (s, 2H), 1.40 (s, 9H).

Example 15

Preparation of Compound 15

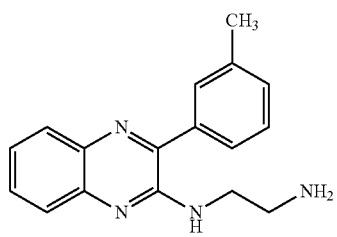 [SMILES: Cc1cccc(-c2nc3ccccc3nc2NCCN)c1]

To a solution of 2-chloro-3-(m-tolyl)quinoxaline 15a (50 mg, 197 mmol) in 2 ml ACN was added excess ethylene diamine (0.1 ml) and the resulting solution was stirred at room temperature overnight. The solvents were removed and the residue was purified in ISCO. Elution with CH$_2$Cl$_2$ to (10/89/1:MeOH/CHCl$_3$/ammonium hydroxide) afforded the desired compound (38 mg, 69% yield). $^1$H NMR (300 MHz, CDCl$_3$) δ 7.93 (d, J=8.1 Hz, 1H), 7.74 (d, J=8.1 Hz, 1H), 7.61-7.51 (m, 3H), 7.47-7.33 (m, 3H), 5.62 (bs, 1H), 3.64 (qt, 2H), 3.02 (t, J=5.7 Hz, 2H), 2.47 (s, 3H), The requisite intermediate was prepared as follows:
a. Preparation of Compound 15a

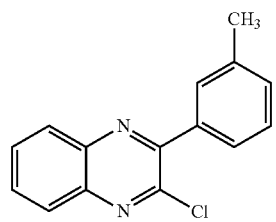 [SMILES: Cc1cccc(-c2nc3ccccc3nc2Cl)c1]

A mixture of commercially available 2,3-dichloroquinoxaline (800 mg, 4.0 mm01), 3-methyl phenylboronic acid (880 mg, 4.4 mmol), Cs$_2$CO$_3$ (2.5 g), PCy$_3$ (42 mg) and Pd$_2$(dba)$_3$ in dioxane (10 mL) under nitrogen was refluxed for 24 hours. After cooled to room temperature, the reaction mixture was diluted with EtOAc (100 mL) and washed with saturated NaHCO$_3$ (30 mL), brine (30 mL), dried over Na$_2$SO$_4$. The organic layer was concentrated under reduced pressure and purified on silica gel. Elution with EtOAc/hexanes solvent system afforded compound 15a (300 mg, 30% yield). $^1$H NMR (300 MHz, CDCl$_3$) δ 8.20-8.16 (m, 1H), 8.11-8.07 (m, 1H), 7.85-7.80 (m, 2H), 7.66 (m, 2H), 7.44 (t, J=6.0 Hz, 1H), 7.36 (d, J=7.5 Hz, 1H), 2.49 (s, 3H).

Example 16

Preparation of Compound 16

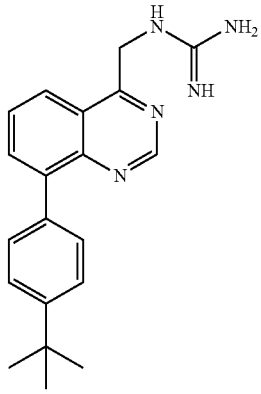 [SMILES: CC(C)(C)c1ccc(-c2cccc3c(CNC(=N)N)ncnc23)cc1]

A 10-mL vial was added di-tert-butyl guanidine compound 16e (40 mg, 0.075 mmol), CH$_2$Cl$_2$ (1.0 mL), and TFA (1.0 mL). The sealed vial was stirred at rt overnight. The solvent was removed and the residue was purified on silica gel. Elution with CH$_2$Cl$_2$ to (10/89/1:MeOH/CHCl$_3$/ammonium hydroxide) afforded the title compound as white solid (14 mg, 56% yield). $^1$HNMR (400 MHz, CDCl$_3$) δ 9.14 (s, 1H), 8.62 (bs, 1H), 8.01 (d, J=8.0 Hz, 1H), 7.88 (d, J=8.0 Hz, 1H), 7.65 (m, 1H), 7.49 (m, 7H), 4.91 (s, 2H), 1.35 (s, 9H).

The requisite intermediates were prepared as follows:

a. Preparation of Compound 16a

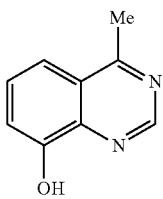 [SMILES: Cc1ncnc2c(O)cccc12]

Prepared following a literature method: PCT Int. Appl. 2004014871, February 2004.

b. Preparation of Compound 16b

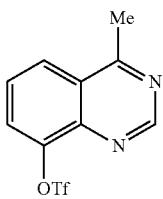 [SMILES: Cc1ncnc2c(OS(=O)(=O)C(F)(F)F)cccc12]

To a solution of 4-methylquinazolin-8-ol 16a (130 mg, 0.812 mmol), Et$_3$N (0.17 mL) in 5.0 mL DCM was added Tf$_2$O (0.16 mL, 0.975 mmol) at −78° C. and the reaction mixture was stirred for 1.5 h. After warming to room temperature, the reaction mixture was diluted with DCM, washed with NaHCO$_3$, dried, and concentrated to give the crude product. Purification in ISCO using 0-40% ethyl acetate in hexane produced the pure triflate (168 mg, 71% yield). $^1$H NMR (CDCl$_3$, 400 MHz) δ 9.31 (s, 1H), 8.15 (d, J=8.4 Hz, 1H), 7.79 (d, J=7.8 Hz, 1H), 7.68 (m, 1H), 3.00 (s, 1H).

c. Preparation of Compound 16c

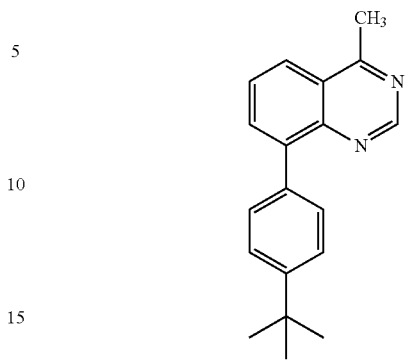

A 25-mL round bottom flask equipped with a magnetic stirrer, a condenser and a nitrogen in/outlet adapter was charged with triflate 16b (100 mg, 0.342 mmol), 4-tert-butylphenylboronic acid (91 mg, 0.511 mmol), DME (4.0 ml), Na$_2$CO$_3$ (1.5 mL, 2M). The resulting solution was degassed for 15 min, then Pd(PPh$_3$)$_4$ (40 mg, 0.034 mmol) was added. The reaction mixture was warmed to 80° C. and stirred for 1 h. After cooled to room temperature, the reaction mixture was diluted with EtOAc and washed with saturated NaHCO$_3$, brine, dried over Na$_2$SO$_4$. The organic layer was concentrated under reduced pressure and purified on silica gel. Elution with EtOAc/hexanes solvent system afforded the desired compound (86 mg, 91% yield). $^1$H NMR (CDCl$_3$, 400 MHz) δ 9.21 (s, 1H), 8.09 (dd, J=8.4, 1.4 Hz, 1H), 7.90 (dd, J=7.2, 1.4 Hz, 1H), 7.69-7.64 (m, 1H), 7.63 (d, J=8.0 Hz, 2H), 7.52 (d, J=8.0 Hz, 2H), 2.99 (s, 3H), 1.38 (s, 9H).

d. Preparation of Compound 16d

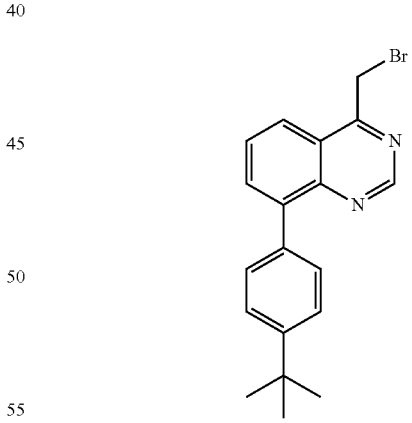

A mixture of substituted quinazoline 16c (80 mg, 0.289 mmol), NBS (57 mg, 0.319 mmol) in carbon tetrachloride (5.0 mL) was heated under light for 1 h. The solids were filtered and the solvent was removed to give the crude product. Purification using 10% ethyl acetate in hexane afforded the product (55 mg, 53% yield) with some dibrominated product. $^1$H NMR (400 MHz, CDCl$_3$) δ 9.31 (s, 1H), 8.19 (dd, J=8.4, 1.3 Hz, 1H), 7.95 (dd, J=7.2, 1.3 Hz, 1H), 7.76 (m, 1H), 7.75 (d, J=8.3 Hz, 2H), 7.53 (d, J=8.4 Hz, 2H), 4.97 (s, 2H), 1.39 (s, 9H).

e. Preparation of Compound 16e

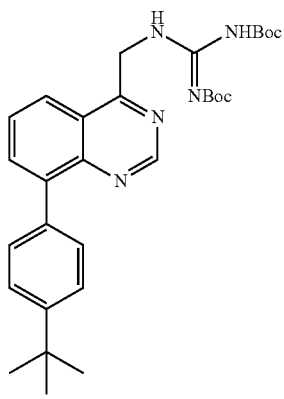

A 25-mL round bottom flask equipped with a magnetic stirrer, a condenser and a nitrogen in/outlet adapter was charged with bromomethyl intermediate 16d (30 mg, 0.084 mmol), DMF (2.0 mL), $K_2CO_3$ (23 mg, 0.169 mmol), and 1,3-bis(tert-butoxycarbonyl)guanidine (26 mg, 0.10 mmol) The reaction mixture was stirred at 50° C. for 16 h. The reaction mixture was diluted with EtOAc, washed with water, 10% LiCl, brine, dried over $Na_2SO_4$, concentrated, and purified on silica gel. Elution with 50% EtOAc/hexanes afforded the title compound as a white solid (44 mg, 98% yield). $^1$H NMR (400 MHz, $CDCl_3$) δ 9.54 (bs, 2H), 9.25 (s, 1H), 8.05 (dd, J=8.4, 1.3 Hz, 1H), 7.93 (dd, J=7.2, 1.3 Hz, 1H), 7.7 (m, 1H), 7.64 (d, J=8.4 Hz, 2H), 7.53 (d, J=8.4 Hz, 2H), 5.94 (s, 2H), 1.42 (s, 9H), 1.38 (s, 9H), 1.16 (s, 9H).

Example 17

Preparation of Compound 17

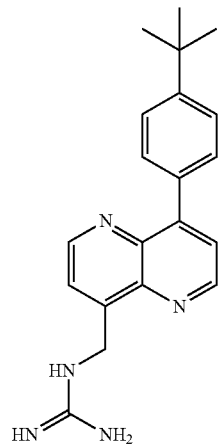 [SMILES: CC(C)(C)c1ccc(-c2ccnc3c(CNC(=N)N)ccnc23)cc1]

A 10-mL vial was added di-tert-butyl guanidine compound 17e (25 mg, 0.047 mmol), $CH_2Cl_2$ (0.5 mL), and TFA (0.5 mL). The sealed vial was stirred at rt overnight. The solvent was removed and the residue was purified on silica gel. Elution with $CH_2Cl_2$ to (10/89/1:MeOH/$CHCl_3$/ammonium hydroxide) afforded the desired compound as white solid (5 mg, 32% yield). $^1$H NMR (300 MHz, $CD_3OD$) δ 9.04 (d, J=4.5 Hz, 1H), 8.95 (d, J=3.9 Hz, 1H), 7.81 (d, J=4.2 Hz, 1H), 7.69 (m, 3H), 7.59 (d, J=8.7 Hz, 2H), 5.12 (s, 2H), 1.40 (s, 9H).

The requisite intermediates were prepared as follows:
a. Preparation of Compound 17a

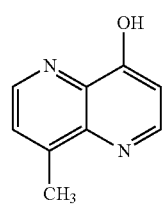

Prepared by following literature method: Journal of the American Chemical Society, 131 (2), 763-777, 2009.

b. Preparation of Compound 17b

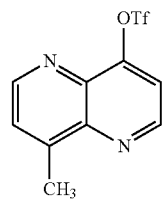

To a solution of 8-methyl-1,5-napthyridin-4-ol 17a (165 mg, 1.03 mmol), $Et_3N$ (0.21 mL) in 4.0 mL DCM was added $Tf_2O$ (0.210 mL, 1.24 mmol) at 0° C. and the reaction mixture was stirred for 1 h. After warming to room temperature, the reaction mixture was diluted with DCM, washed with $NaHCO_3$, dried, and concentrated to give the crude product. Purification in ISCO using 10% MeOH in DCM produced the pure triflate (160 mg, 53% yield). $^1$H NMR ($CDCl_3$, 300 MHz) δ 9.03 (d, J=4.8, 1H), 8.94 (d, J=4.5 Hz, 1H), 7.60 (d, J=4.2 Hz, 1H), 7.52 (d, J=4.5 Hz, 1H), 2.87 (s, 3H).

c. Preparation of Compound 17c

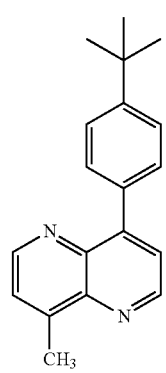 [SMILES: Cc1ccnc2c(-c3ccc(C(C)(C)C)cc3)ccnc12]

A 25-mL round bottom flask equipped with a magnetic stirrer, a condenser and a nitrogen in/outlet adapter was charged with triflate 17b (84 mg, 0.287 mmol), 4-tert-butylphenylboronic acid (77 mg, 0.43 mmol), DME (3.2 ml), $Na_2CO_3$ (1.3 mL, 2.0M). The resulting solution was degassed for 15 min, then $Pd(PPh_3)_4$ (33 mg, 0.03 mmol) was added. The reaction mixture was warmed to 80° C. and stirred for 1 h. After cooled to room temperature, the reaction mixture was diluted with EtOAc and washed with saturated $NaHCO_3$, brine, dried over $Na_2SO_4$. The organic layer was concentrated under reduced pressure and purified on silica gel. Elution with EtOAc/hexanes solvent system afforded the desired compound (80 mg, 100% yield). ¹H NMR (300 MHz, CDCl₃) δ 9.02 (d, J=4.5 Hz, 1H), 8.89 (d, J=4.5 Hz, 1H), 7.76 (d, J=6.6 Hz, 2H), 7.65 (d, J=4.2 Hz, 1H), 7.58 (d, J=8.4 Hz, 2H), 7.50 (d, J=4.2 Hz, 1-H), 2.91 (s, 3H), 1.41 (s, 9H).

d. Preparation of Compound 17d

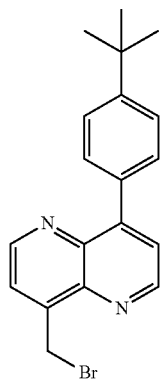 [SMILES: CC(C)(C)c1ccc(-c2ccnc3c(CBr)ccnc23)cc1]

A mixture of substitited napthayridine 17c (80 mg, 0.29 mmol), NBS (68 mg, 0.376 mmol) in carbon tetrachloride (10.0 mL) was heated under light for 1 h. The solids were filtered and the solvent was removed to give the crude product. Purification using 0-50% ethyl acetate in hexane afforded the product (50 mg, 49% yield) along with some dibrominated product. ¹H NMR (300 MHz, CDCl₃) 9.07 (d, J=4.2 Hz, 1H), 9.02 (d, J=4.5 Hz, 1-H), 7.77-7.70 (m, 4H), 7.59 (d, J=8.4 Hz, 2H), 5.25 (s, 2H), 1.42 (s, 9H).

e. Preparation of Compound 17e

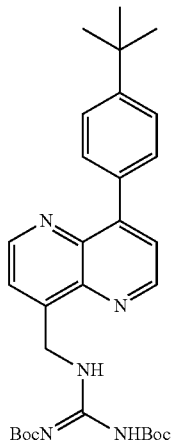

A 25-mL round bottom flask equipped with a magnetic stirrer, a condenser and a nitrogen in/outlet adapter was charged with bromomethyl intermediate 17d (25 mg, 0.070 mmol), DMF (2 mL), K₂CO₃ (20 mg, 0.14 mmol), and 1,3-bis(tert-butoxycarbonyl)guanidine (27 mg, 0.11 mmol) The reaction mixture was stirred at 50° C. for 16 h. The reaction mixture was diluted with EtOAc, washed with water, 10% LiCl, brine, dried over Na₂SO₄, concentrated, and purified on silica gel. Elution with 100% EtOAc afforded the desired compound as a white solid (27 mg, 70% yield). ¹H NMR (300 MHz, CDCl₃) 9.5 (bs, 2H), 8.96-8.93 (m, 2H), 7.74 (d, J=8.1 Hz, 2H), 7.65-7.63 (m, 1H), 7.55 (d, J=8.1 Hz, 2H), 7.32 (d, J=4.2 Hz, 1H), 5.98 (s, 2H), 1.42 (s, 9H), 1.38 (s, 9H), 1.16 (s, 9H).

Example 18

Preparation of Compound 18

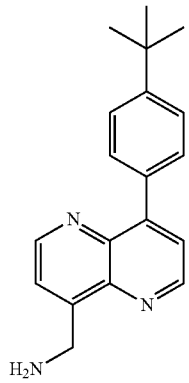

To a solution of azide 18a (9 mg, 0.028 mmol) in 0.9 mL THF and 0.1 mL H₂O was added polymer supported PPh₃ (47 mg) and the mixture was stirred for 16 h. The solid was filtered off and the solvents were removed under vacuuo. The resulting residue was dissolved in MeOH and was purified in ISCO eluting with CH₂Cl₂ to (10/89/1:MeOH/CHCl₃/ammonium hydroxide) which afforded the title compound as white solid (4 mg, 49% yield). ¹H NMR (300 MHz, CDCl₃) δ 9.06 (m, 1H), 9.0 (m, 1H), 7.8 (m, 4H), 7.64 (m, 2H), 5.15 (s, 2H), 1.43 (s, 9H).

The requisite intermediates were prepared as follows:

a. Preparation of Compound 18a

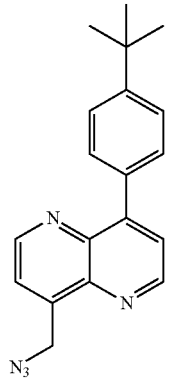 [SMILES: CC(C)(C)c1ccc(-c2ccnc3c(CN=[N+]=[N-])ccnc23)cc1]

To a solution of the bromide 17d (17 mg, 0.048 mmol) in 1.0 mL DMF was added NaN₃ (5.5 mg, 0.085 mmol) and the reaction mixture was stirred for 12 h. After the completion of the reaction, the solvent was removed, the residue was diluted with ethyl acetate and was washed with NaHCO₃ and brine provided the product (9 mg, 60% yield) used as crude for the reduction step.

Example 19

Preparation of Compound 19

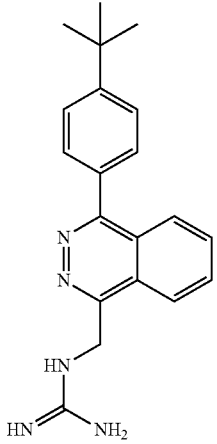 [SMILES: CC(C)(C)c1ccc(-c2nnc(CNC(=N)N)c3ccccc23)cc1]

A 10-mL vial was added di-tert-butyl guanidine compound 19e (20 mg, 0.037 mmol), $CH_2Cl_2$ (0.5 mL), and TFA (0.5 mL). The sealed vial was stirred at rt overnight. The solvent was removed and the residue was purified on silica gel. Elution with $CH_2Cl_2$ to (10/89/1:MeOH/$CHCl_3$/ammonium hydroxide) afforded the title compound as white solid (7 mg, 57% yield). $^1$H NMR (300 MHz, $CD_3OD$) δ 8.39 (d, J=8.1 Hz, 1H), 8.29-8.23 (m, 2H), 8.15 (m, 1H), 7.77-7.70 (m, 4H), 5.30 (s, 2H), 1.44 (s, 9H).

The requisite intermediates were prepared as follows.

a. The Intermediate 19a

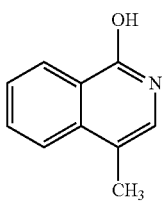

is commercially available.

b. Preparation of Compound 19b

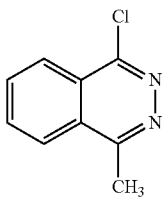

A mixture of 4-methylpthalazin-1-ol 19a (200 mg, 1.25 mmol) in 2.0 mL $POCl_3$ was heated in a sealed tube at 115° C. for 2 h. The reaction mixture was cooled down and the residue was purified in ISCO using 0-50% EtOAC in hexane to afford the desired product (150 mg, 85% yield). $^1$H NMR ($CDCl_3$, 300 MHz) δ 8.34 (m, 1H), 8.11 (m, 1H), 8.02 (m, 2H), 3.08 (s, 3H).

c. Preparation of Compound 19c

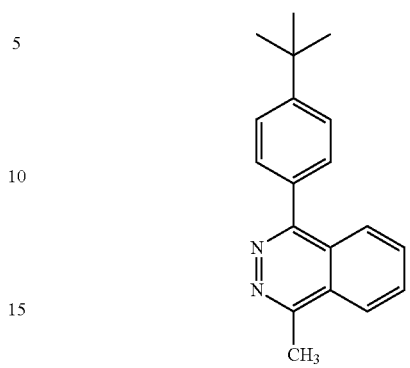

A 25-mL round bottom flask equipped with a magnetic stirrer, a condenser and a nitrogen in/outlet adapter was charged with 1-chloro-4-methylpthalazine 19b (150 mg, 0.843 mmol), 4-tert-butylphenylboronic acid (225 mg, 1.26 mmol), DME (10 mL), $Na_2CO_3$ (3.8 mL, 2M). The resulting solution was degassed for 15 min, then $Pd(PPh_3)_4$ (93 mg, 0.084 mmol) was added. The reaction mixture was warmed to 100° C. and stirred for 3 h. After cooled to room temperature, the reaction mixture was diluted with EtOAc and washed with saturated $NaHCO_3$, brine, dried over $Na_2SO_4$. The organic layer was concentrated under reduced pressure and purified on silica gel. Elution with EtOAc/hexanes solvent system afforded the desired compound (150 mg, 64% yield). $^1$H NMR (300 MHz, $CD_3OD$) δ 8.34 (m, 1H), 8.09-7.97 (m, 3H), 7.69-7.62 (m, 4H), 3.04 (s, 3H), 1.42 (s, 9H).

d. Preparation of Compound 19d

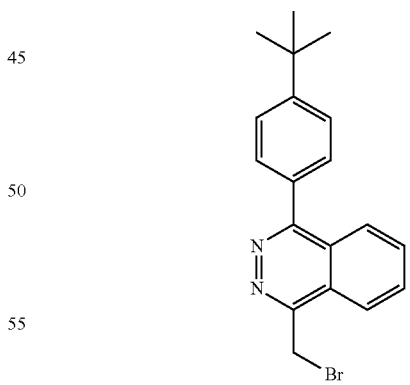

A mixture of substitited pthalazine 19c (150 mg, 0.543 mmol), NBS (147 mg, 0.815 mmol) in carbon tetrachloride (2.0 mL) was heated under light for 2 h. The solids were filtered and the solvent was removed to give the crude product. Purification using 0-50% ethyl acetate in hexane afforded the product along with some dibrominated product and some starting material as a mixture. This mixture was used for next step without further separation.

e. Preparation of Compound 19e

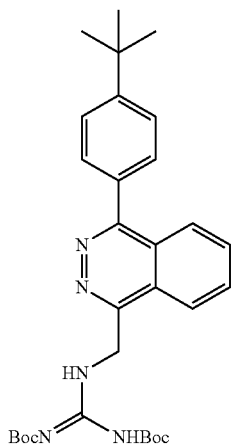

A 25-mL round bottom flask equipped with a magnetic stirrer, a condenser and a nitrogen in/outlet adapter was charged with above mixture 19d (23 mg, 0.059 mmol), DMF (1.0 mL), $K_2CO_3$ (16 mg, 0.118 mmol), and 1,3-bis(tert-butoxycarbonyl)guanidine (23 mg, 0.089 mmol) The reaction mixture was stirred at 50° C. for 16 h. The reaction mixture was diluted with EtOAc, washed with water, 10% LiCl, brine, dried over $Na_2SO_4$, concentrated, and purified on silica gel. Elution with 5% EtOAc/hexanes afforded the title compound as a white solid (20 mg). $^1$H NMR (300 MHz, $CDCl_3$) δ 9.55 (bs, 2H), 8.21-8.14 (m, 2H), 7.88 (m, 2H), 7.71 (d, J=8.4 Hz, 2H), 7.58 (d, J=8.1 Hz, 2H), 5.98 (s, 2H), 1.42-1.22 (9H×3).

Example 20

Preparation of Compound 20

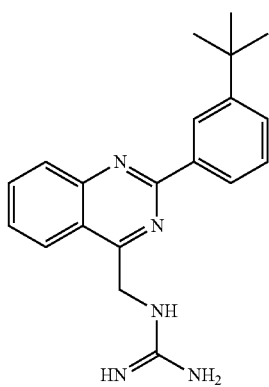 [SMILES: CC(C)(C)c1cccc(-c2nc(CNC(=N)N)c3ccccc3n2)c1]

A 10-mL vial was added di-tert-butyl guanidine compound 20d (40 mg, 0.075 mmol), $CH_2Cl_2$ (1.0 mL), and TFA (1.0 mL). The sealed vial was stirred at rt overnight. The solvent was removed and the residue was purified on silica gel. Elution with $CH_2Cl_2$ to (10/89/1:MeOH/$CHCl_3$/anunonium hydroxide) afforded the desired compound as white solid (12 mg, 48% yield). $^1$H NMR (300 MHz, $CD_3OD$) δ 8.73 (t, J=1.8 Hz, 1H), 8.48 (dt, J=8.1, 1.5 Hz, 1H), 8.21-8.12 (m, 2H), 8.04-7.98 (m, 1H), 7.77-7.71 (m, 1H), 7.63-7.59 (m, 1H), 7.48 (t, J=7.8 Hz, 1H), 5.25 (s, 2H), 1.44 (s, 9H).

The requisite intermediates were prepared as follows.

a. The Compound 20a

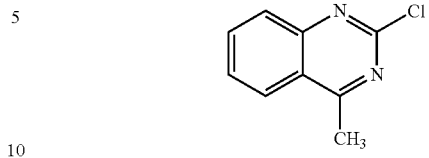

is commercially available.

b. Preparation of Compound 20b

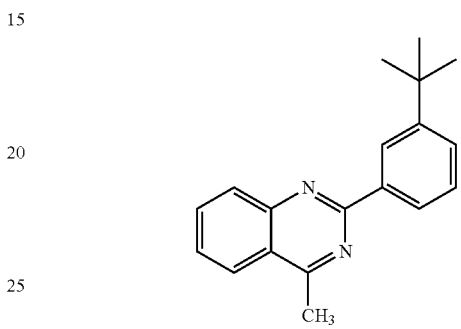

A 25-mL round bottom flask equipped with a magnetic stirrer, a condenser and a nitrogen in/outlet adapter was charged with 2-chloro-4-methylquinazoline 20a (250 mg, 1.4 mmol), 3-tert-butylphenylboronic acid (373 g, 2.1 mmol), DME (16 ml), $Na_2CO_3$ (6.3 mL, 2.0M). The resulting solution was degassed for 15 min, then $Pd(PPh_3)_4$ (161 mg, 0.14 mmol) was added. The reaction mixture was warmed to 85° C. and stirred for 5 h. After cooled to room temperature, the reaction mixture was diluted with EtOAc and washed with saturated $NaHCO_3$, brine, dried over $Na_2SO_4$. The organic layer was concentrated under reduced pressure and purified on silica gel. Elution with EtOAc/hexanes solvent system afforded the desired compound (243 mg, 63% yield). $^1$H NMR (300 MHz, $CDCl_3$) δ 8.66 (s, 1H), 8.42 (d, J=7.5 Hz, 1H), 8.08 (d, J=9.0 Hz, 2H), 7.86 (t, J=7.2 Hz, 1H), 7.60-7.43 (m, 3H), 3.02 (s, 3H), 1.43 (s, 9H).

c. Preparation of Compound 20c

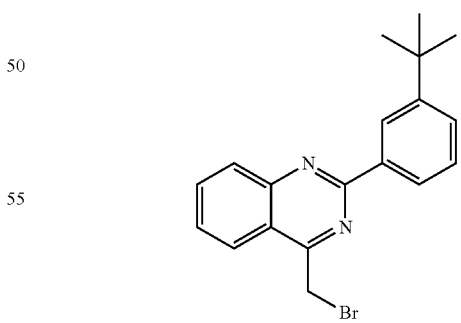

A mixture of substituted 4-methylquinazoline 20b (223 mg, 0.808 mmol), NBS (380 mg, 2.1 mmol) in carbon tetrachloride (3.0 mL) was heated under light for 16 h. The solids were filtered and the solvent was removed to give the crude product. Purification using 10% ethyl acetate in hexane afforded the product (311 mg) as a mixture with some dibrominated product and some starting material. This material was used for the next step without further purification.

d. Preparation of Compound 20d

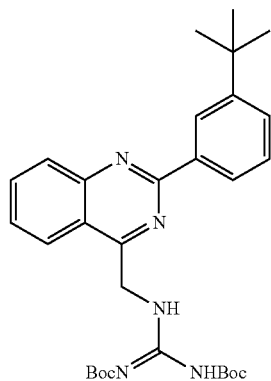

A 25-mL round bottom flask equipped with a magnetic stirrer, a condenser and a nitrogen in/outlet adapter was charged with above bromide mixture 20c (144 mg, 0.41 mmol), DMF (2 mL), $K_2CO_3$ (112 mg, 0.811 mmol), and 1,3-bis(tert-butoxycarbonyl)guanidine (156 mg, 0.61 mmol) The reaction mixture was stirred at 50° C. for 2 h. The reaction mixture was diluted with EtOAc, washed with water, 10% LiCl, brine, dried over $Na_2SO_4$, concentrated, and purified on silica gel. Elution with 0-50% EtOAc/hexanes afforded the title compound as a white solid (45 mg). $^1$H NMR (300 MHz, $CDCl_3$) δ 9.75 (bs, 2H), 8.70 (t, J=1.3 Hz, 1H), 8.41 (dt, J=5.8, 1.0 Hz, 1H), 8.09 (d, J=6.2 Hz, 1H), 8.02 (d, J=5.8 Hz, 1H), 7.88-7.84 (m, 1H), 7.59-7.50 (m, 1H), 7.49 (m, 1H), 7.42 (t, J=5.8 Hz, 1H), 5.94 (s, 2H), 1.39 (s, 18H), 1.23 (s, 9H).

Example 21

Preparation of Compound 21

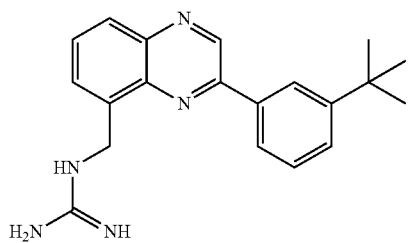 [SMILES: CC(C)(C)c1cccc(-c2cnc3cccc(CNC(=N)N)c3n2)c1]

A 10-mL vial was added di-tert-butyl guanidine compound 21d (85 mg, 0.159 mmol), $CH_2Cl_2$ (1 mL), and TFA (1 mL). The sealed vial was stirred at rt overnight. The solvent was removed and the residue was purified on silica gel. Elution with $CH_2Cl_2$ to (10/89/1:MeOH/$CHCl_3$/ammonium hydroxide) afforded the desired compound (47 mg, 87% yield); $^1$H NMR (300 MHz, $CD_3OD$) δ 9.55 (s, 1H), 8.41 (t, J=1.5 Hz, 1H), 8.17-8.40 (m, 2H), 7.88 (m, 2H), 7.67 (m, 1H), 7.58 (t, J=7.8 Hz, 1H), 5.15 (s, 2H), 1.47 (s, 9H).

The requisite intermediates were prepared as follows:

a. Preparation of Compound 21a

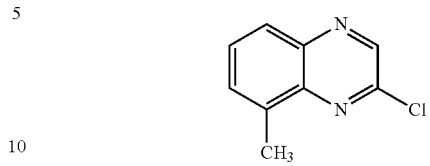

Prepared by following literature method: PCT Int. Appl. 2007107965, 27 Sep. 2007, Hubschwerlen, Christian, Rueedi, Georg, Surivet Jean-Philippe, Zumbrunn Acklin, Cornelia b. Preparation of Compound 21b

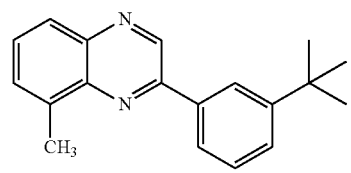 [SMILES: Cc1cccc2ncc(-c3cccc(C(C)(C)C)c3)nc12]

A 50-mL round bottom flask equipped with a magnetic stirrer, a condenser and a nitrogen in/outlet adapter was charged with 2-chloro-8-methylquinoxaline 21a (340 mg, 1.8 mmol), 3-tert-butylphenylboronic acid (605 mg, 3.4 mmol), water/dioxane (1 mL/3 ml), $K_2CO_3$ (470 mg, 3.4 mmol). The resulting solution was degassed for 5 min, then $Pd(PPh_3)_4$ (80 mg) was added. The reaction mixture was warmed to 100° C. and stirred for 3 h. After cooled to room temperature, the reaction mixture was diluted with EtOAc (100 mL) and washed with saturated $NaHCO_3$ (30 mL), brine (30 mL), dried over $Na_2SO_4$. The organic layer was concentrated under reduced pressure and purified on silica gel. Elution with EtOAc/hexanes solvent system afforded the title compound 21b (150 mg, 30% yield). LC/MS 277.13 (M+H).

c. Preparation of Compound 21c

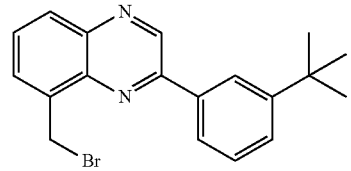 [SMILES: CC(C)(C)c1cccc(-c2cnc3cccc(CBr)c3n2)c1]

A mixture of substituted quinoxaline 21b (130 mg, 0.47 mmol), NBS (92 mg, 0.518 mmol) in carbon tetrachloride (5.0 mL) was heated under light for 2 h. The solids were filtered and the solvent was removed to give the crude product. Purification using 10% ethyl acetate in hexane afforded the product 21c (75 mg, 45% yield). $^1$H NMR (300 MHz, $CDCl_3$) δ 9.38 (s, 1H), 8.37 (s, 1H), 8.11-8.06 (m, 2H), 7.88 (d, J=6.9 Hz, 1H), 7.70 (t, J=7.2 Hz, 1H), 7.59-7.5 (m, 2H), 5.27 (s, 2H), 1.44 (s, 9H).

d. Preparation of Compound 21d

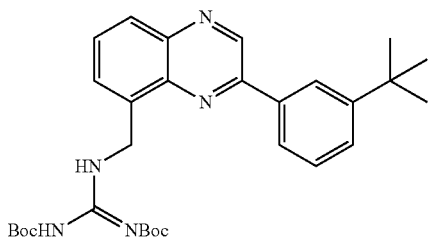

A 25-mL round bottom flask equipped with a magnetic stirrer was charged with bromomethyl intermediate 21c (110 mg, 0.309 mmol), DMF (4 mL), K$_2$CO$_3$ (85 mg, 0.618 mmol), and 1,3-bis(tert-butoxycarbonyl)guanidine (103 mg, 0.403 mmol) The reaction mixture was stirred at 50° C. for 2 hours. The reaction mixture was diluted with EtOAc, washed with water (10 mL), 10% LiCl, brine, dried over Na$_2$SO$_4$, concentrated, and purified on silica gel. Elution with 5% EtOAc/hexanes afforded the title compound as a white solid 1,3-bis(t-butoxycarbonyl)-guanidine 21d (100 mg, 61% yield). $^1$H NMR (300 MHz, CDCl$_3$) δ 9.6 (bs, 1H), 9.45 (bs, 1H), 9.36 (s, 1H), 8.28 (s, 1H), 8.06-8.98 (m, 2H), 7.68 (t, J=8.1 Hz, 1H), 7.56-7.47 (m, 3H), 6.04 (s, 2H), 1.42-1.12 (3×9H).

Example 22

Preparation of Compound 22

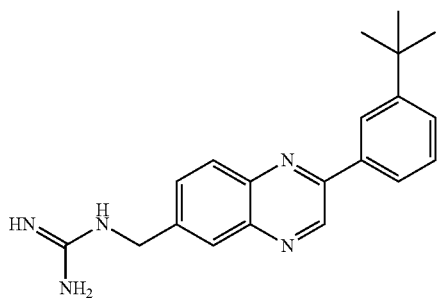 [SMILES: CC(C)(C)c1cccc(-c2cnc3cc(CNC(=N)N)ccc3n2)c1]

A 10-mL vial was added di-tert-butyl guanidine compound 22d (90 mg, 0.168 mmol), CH$_2$Cl$_2$ (1 mL), and TFA (1 mL). The sealed vial was stirred at room temperature overnight. The solvent was removed and the residue was purified on silica gel. Elution with CH$_2$Cl$_2$ to (10/89/1: MeOH/CHCl$_3$/ammonium hydroxide) afforded the desired compound (50 mg, 91% yield). LCMS: 334.05

The requisite intermediates were prepared as follows:
a. Preparation of Compound 22a

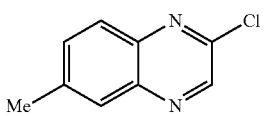 [SMILES: Cc1ccc2nc(Cl)cnc2c1]

The compound was prepared as described by Fahr, Bruce T., et al., *Bioorganic & Medicinal Chemistry Letters*, 2006, 16(3), 559-562.

b. Preparation of Compound 22b

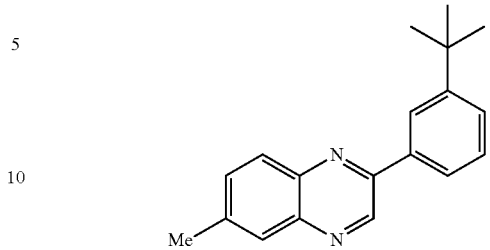

A 50-mL round bottom flask equipped with a magnetic stirrer, a condenser and a nitrogen in/outlet adapter was charged with 2-chloro-6-methylquinoxaline 22a (250 mg, 1.4 mmol), 3-tert-butylphenylboronic acid (400 mg, 2.1 mmol), water/dioxane (1 mL/3 ml), K$_2$CO$_3$ (386 mg, 2.8 mmol). The resulting solution was degassed for 5 min, then Pd(PPh$_3$)$_4$ (30 mg) was added. The reaction mixture was warmed to 100° C. and stirred for 3 hours. After cooled to room temperature, the reaction mixture was diluted with EtOAc and washed with saturated NaHCO$_3$, brine, dried over Na$_2$SO$_4$. The organic layer was concentrated under reduced pressure and purified on silica gel. Elution with EtOAc/hexanes solvent system afforded the title compound 22b as oil (280 mg, 72% yield). LC/MS 277.13 (M+H).

c. Preparation of Compound 22c

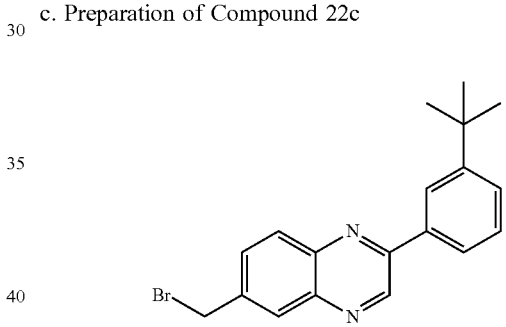

A mixture of substituted quinoxaline 22b (270 mg, 1.1 mmol), NBS (213 mg, 1.2 mmol) in carbon tetrachloride (5.0 mL) was heated under light for 2 hours. The solids were filtered and the solvent was removed to give the crude product. Purification using 10% ethyl acetate in hexane afforded the product 22c as a mixture of monobromo, dibromo and some starting material which was used for the next step.

d. Preparation of Compound 22d

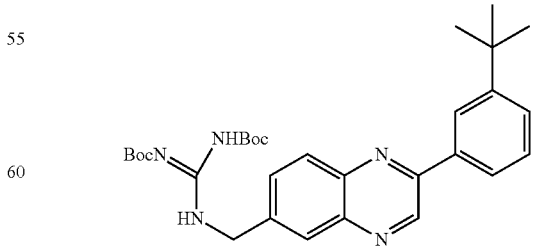

A 25-mL round bottom flask equipped with a magnetic stirrer was charged with 22c and its dibromo derivative (200 mg), DMF (5 mL), K$_2$CO$_3$ (200 mg), and 1,3-bis(tert-butoxycarbonyl)guanidine (200 mg) The reaction mixture was stirred at 50° C. for 2 hours. The reaction mixture was diluted with EtOAc, washed with water (10 mL), 10% LiCl, brine, dried over Na$_2$SO$_4$, concentrated, and purified on silica gel. Elution with 5% EtOAc/hexanes afforded the desired compound 22d (110 mg).

Example 23

The following can illustrate representative pharmaceutical dosage forms, containing a compound of formula I ('Compound X') or a pharmaceutically acceptable salt thereof, for therapeutic or prophylactic use in humans.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
| --- | --- |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
| --- | --- |
| Compound X = (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
| --- | --- |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating a bacterial infection in a mammal comprising administering to the mammal an effective amount of a bicyclic heteroaromatic ring compound of formulae selected from:

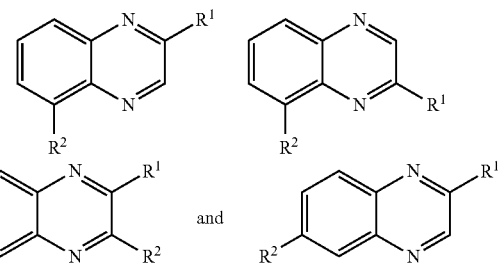

Wherein:
R$^1$ is phenyl that is substituted with one or more groups independently selected from halo, (C$_1$-C$_6$)alkyl, (C$_1$-C$_6$)alkoxycarbonyl, —C(=O)NR$^e$R$^f$, and phenyl that is optionally substituted with one or more halo, or (C$_1$-C$_6$)alkyl,
R$^2$ is —NR$^c$R$^d$, —N$^+$(R$_3$)Z$^-$, or —NR$^a$C(=NR$^a$)—NR$^c$R$^d$, or R$^2$ is (C$_1$-C$_6$)alkyl that is substituted with —NR$^c$R$^d$, —N$^+$(Ra)$_3$ Z$^-$, —NR$^a$C(=NR$^a$)—NR$^c$R$^d$, or —NR$^a$—C(=NR$^a$)—R$^a$,
each R$^a$ is independently H, or (C$_1$-C$_6$)alkyl,
each R$^c$ and R$^d$ is independently selected from H, or (C$_1$-C$_6$)alkyl that is optionally substituted with one or more hydroxy or amino; or R$^c$ and R$^d$ together with the nitrogen to which they are attached form a aziridino, azetidino, morpholino, piperazino, pyrrolidino or piperidino;
each R$^e$ and R$^f$ is independently selected from H, or (C$_1$-C$_6$)alkyl that is optionally substituted with one or more hydroxy or amino; or R$^e$ and R$^f$ together with the nitrogen to which they are attached form a aziridino, azetidino, morpholino, piperazino, pyrrolidino or piperidino;
and each Z$^-$ is independently a suitable counter ion;
or a pharmaceutical acceptable salt thereof.

2. The method of claim 1 wherein R$^1$ is, 3-biphenyl, 3-tert-butylphenyl, 4-tert-butylphenyl, 3-fluorophenyl, 3-methoxycarbonyl-5-(4-tert-butylphenyl)phenyl, 3-aminocarbonyl -5-(4-tert-butylphenyl)phenyl, 3-(N-(2-hydroxyethyl)aminocarbonyl)-5-(4-tert-butylphenyl)phenyl, or 3-methylphenyl.

3. The method of claim 1 wherein R² is guanadinomethyl, 2-aminoethylamino, aminomethyl, —CH₂—NH—C(=NH)—CH₃, or —CH₂—N=C(NH₂)—NH₂.

4. The method of claim 1 wherein the compound is selected from:

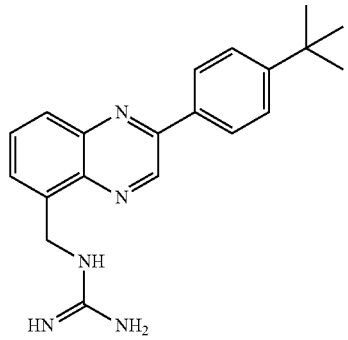

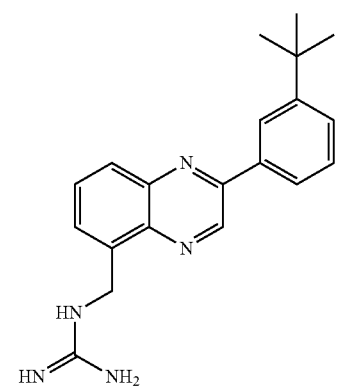

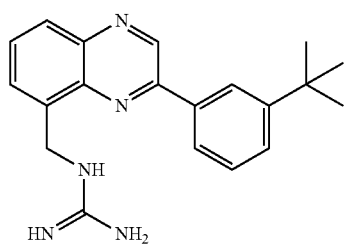

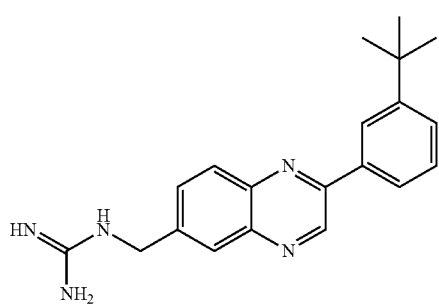

and

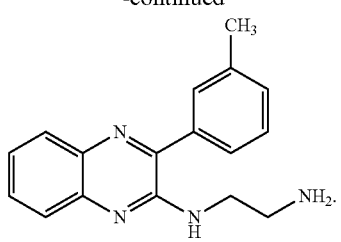

5. The method of claim 1 wherein the compound is:

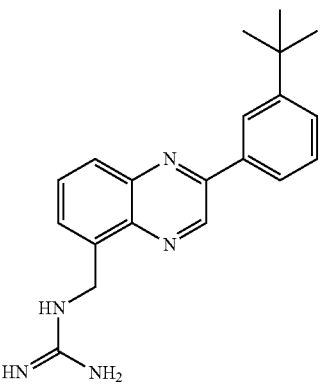 [SMILES: CC(C)(C)c1cccc(-c2cnc3c(CNC(=N)N)cccc3n2)c1]

or a pharmaceutically acceptable salt thereof.

6. A method for treating a bacterial infection in a mammal comprising administering to the mammal an effective amount of compound of formulae selected from:

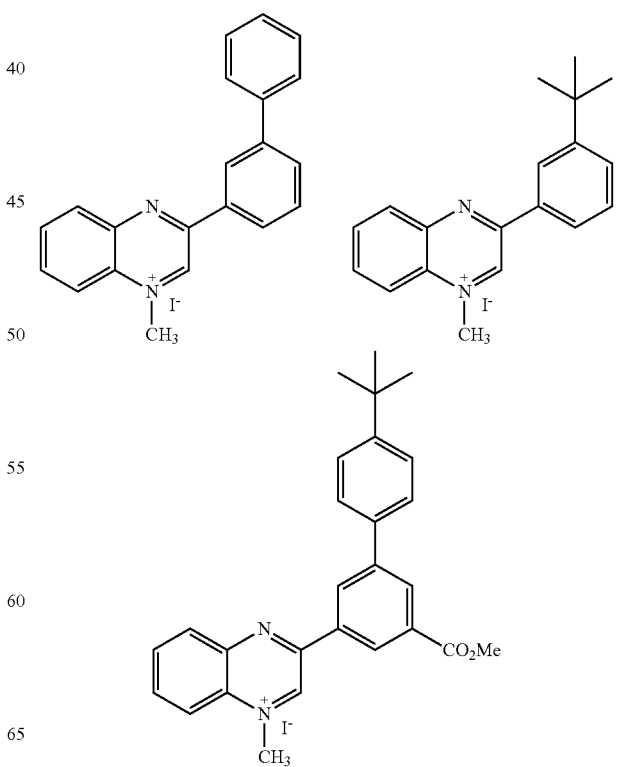

-continued

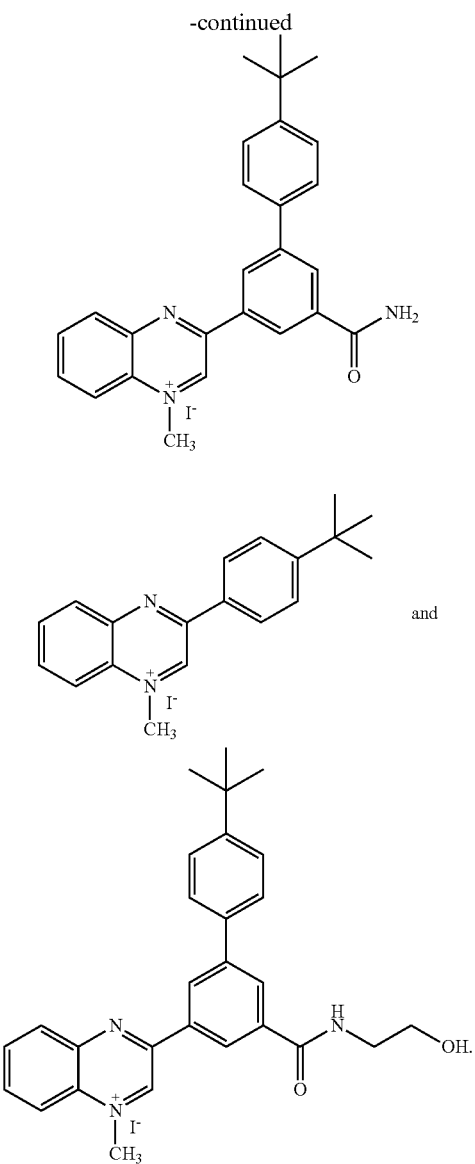

7. The method of claim 1 or claim 5 wherein the bacterial infection is a Gram-negative bacterial strain infection.

8. The method of claim 7 wherein the Gram-negative bacterial strain is selected from the group consisting of *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis* and *Haemophilus influenzae.*

9. The method of claim 1 or claim 5 wherein the bacterial infection is a Gram-positive bacterial strain infection.

10. The method of claim 9 wherein the Gram-positive bacterial strain is selected from the group consisting of *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Mycobacterium tuberculosis, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae* and *Streptococcus salivarius.*

11. The method of claim 1 or claim 5 wherein the bacterial infection is a multiple drug-resistant bacterial strain infection.

12. The method of claim 11 wherein the multiple drug-resistance bacterial strain is selected from the group consisting of methicillin-resistant *Staphylococcus aureus*, vancomycin-resistant *Enterococcus*, multiple drug-resistant tuberculosis and multidrug-resistant *Clostridium difficile.*

* * * * *

UNITED STATES PATENT AND TRADEMARK OFFICE
CERTIFICATE OF CORRECTION

PATENT NO. : 9,822,108 B2
APPLICATION NO. : 14/371950
DATED : November 21, 2017
INVENTOR(S) : Edmond J. LaVoie et al.

It is certified that error appears in the above-identified patent and that said Letters Patent is hereby corrected as shown below:

In the Claims

Column 62, Line 45, Claim 1, please delete "-$N^+(Ra)_3$    $Z^-$," and insert -- -$N^+(R^a)_3Z^-$, -- therefor.

Signed and Sealed this
Eighth Day of May, 2018

Andrei Iancu
*Director of the United States Patent and Trademark Office*